US011241537B2

(12) United States Patent
Jiang et al.

(10) Patent No.: US 11,241,537 B2
(45) Date of Patent: Feb. 8, 2022

(54) CONTEXTUAL PERSONALIZED CLOSED-LOOP ADJUSTMENT METHODS AND SYSTEMS

(71) Applicant: MEDTRONIC MINIMED, INC., Northridge, CA (US)

(72) Inventors: Boyi Jiang, Northridge, CA (US); Yuxiang Zhong, Arcadia, CA (US); Pratik Agrawal, Porter Ranch, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 313 days.

(21) Appl. No.: 16/578,247

(22) Filed: Sep. 20, 2019

(65) Prior Publication Data
US 2021/0085863 A1    Mar. 25, 2021

(51) Int. Cl.
| *A61M 5/172* | (2006.01) |
| *G16H 20/17* | (2018.01) |
| *G16H 40/67* | (2018.01) |
| *A61M 5/145* | (2006.01) |

(52) U.S. Cl.
CPC ........ *A61M 5/1723* (2013.01); *A61M 5/1452* (2013.01); *G16H 20/17* (2018.01); *G16H 40/67* (2018.01); *A61M 2205/50* (2013.01); *A61M 2205/52* (2013.01); *A61M 2205/8206* (2013.01); *A61M 2230/201* (2013.01); *A61M 2230/63* (2013.01)

(58) Field of Classification Search
CPC ............ A61M 5/1723; A61M 5/14244; A61M 5/172; A61M 5/14248; A61M 5/142; A61B 5/14532; A61B 5/4839; G16H 20/17; G16H 20/10
See application file for complete search history.

(56) References Cited

U.S. PATENT DOCUMENTS

| 4,562,751 A | 1/1986 | Nason et al. |
| 4,685,903 A | 8/1987 | Cable et al. |
| 4,755,173 A | 7/1988 | Konopka et al. |
| 5,080,653 A | 1/1992 | Voss et al. |
| 5,097,122 A | 3/1992 | Colman et al. |
| 5,391,250 A | 2/1995 | Cheney, II et al. |
| 5,485,408 A | 1/1996 | Blomquist |

(Continued)

FOREIGN PATENT DOCUMENTS

WO    2013/184896 A1    12/2013

OTHER PUBLICATIONS

International Search Report and Written Opinion of International Application No. PCT/US2020/050960, dated Dec. 8, 2020, 13 pp.

*Primary Examiner* — Manuel A Mendez
(74) *Attorney, Agent, or Firm* — Shumaker & Sieffert, P.A.

(57) ABSTRACT

Infusion devices, systems and related methods of autonomously delivering fluid to a patient are disclosed. One method involves monitoring a current operational context during autonomous operation of the infusion device to deliver fluid to a patient in accordance with an operating mode using an initial value for a control parameter, and in response to identifying an adjusted value for the control parameter associated with the current operational context, autonomously operating the infusion device to deliver the fluid to the patient in accordance with the operating mode using the adjusted value for the control parameter in lieu of the initial value and thereafter reverting the control parameter to the initial value.

20 Claims, 7 Drawing Sheets

(56) References Cited

U.S. PATENT DOCUMENTS

| | | |
|---|---|---|
| 5,505,709 A | 4/1996 | Funderburk et al. |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,088,608 A | 7/2000 | Schulman et al. |
| 6,119,028 A | 9/2000 | Schulman et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,485,465 B2 | 11/2002 | Moberg et al. |
| 6,544,212 B2 | 4/2003 | Galley et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,589,229 B1 | 7/2003 | Connelly et al. |
| 6,591,876 B2 | 7/2003 | Safabash |
| 6,641,533 B2 | 11/2003 | Causey, III et al. |
| 6,659,980 B2 | 12/2003 | Moberg et al. |
| 6,736,797 B1 | 5/2004 | Larsen et al. |
| 6,740,072 B2 | 5/2004 | Starkweather et al. |
| 6,749,587 B2 | 6/2004 | Flaherty |
| 6,752,787 B1 | 6/2004 | Causey, III et al. |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 6,817,990 B2 | 11/2004 | Yap et al. |
| 6,827,702 B2 | 12/2004 | Lebel et al. |
| 6,932,584 B2 | 8/2005 | Gray et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,323,142 B2 | 1/2008 | Pendo et al. |
| 7,399,277 B2 | 7/2008 | Saidara et al. |
| 7,402,153 B2 | 7/2008 | Steil et al. |
| 7,442,186 B2 | 10/2008 | Blomquist |
| 7,602,310 B2 | 10/2009 | Mann et al. |
| 7,621,893 B2 | 11/2009 | Moberg et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 8,474,332 B2 | 7/2013 | Bente, IV |
| 8,674,288 B2 | 3/2014 | Hanson et al. |
| 2006/0031094 A1 | 2/2006 | Cohen et al. |
| 2007/0123819 A1 | 5/2007 | Mernoe et al. |
| 2010/0160861 A1 | 6/2010 | Causey, III et al. |
| 2013/0035575 A1 | 2/2013 | Mayou et al. |
| 2013/0338630 A1 | 12/2013 | Agrawal et al. |
| 2014/0066889 A1 | 3/2014 | Grosman et al. |
| 2017/0053084 A1 | 2/2017 | McMahon et al. |
| 2018/0169334 A1 | 6/2018 | Grosman et al. |
| 2019/0321553 A1 | 10/2019 | Grosman et al. |

CONTEXTUAL PERSONALIZED CLOSED-LOOP ADJUSTMENT METHODS AND SYSTEMS

TECHNICAL FIELD

Embodiments of the subject matter described herein relate generally to medical devices, and more particularly, embodiments of the subject matter relate to adjusting personalized settings of an infusion device for diabetes therapy management.

BACKGROUND

The pancreas of a normal healthy person produces and releases insulin into the blood stream in response to elevated blood plasma glucose levels. Beta cells ((3-cells), which reside in the pancreas, produce and secrete the insulin into the blood stream, as it is needed. If (3-cells become incapacitated or die, a condition known as Type I diabetes mellitus (or in some cases if (3-cells produce insufficient quantities of insulin, Type II diabetes), then insulin must be provided to the body from another source. Diabetes affects approximately eight percent of the total population in the United States alone.

Traditionally, because insulin cannot be taken orally, it has been injected with a syringe. Infusion pump devices and systems are relatively well known in the medical arts, for use in delivering or dispensing an agent, such as insulin or another prescribed medication, to a patient. A typical infusion pump includes a pump drive system which typically includes a small motor and drive train components that convert rotational motor motion to a translational displacement of a plunger (or stopper) in a reservoir that delivers medication from the reservoir to the body of a user via a fluid path created between the reservoir and the body of a user. Use of infusion pump therapy has been increasing, especially for delivering insulin for diabetics. For example, external infusion pumps are worn on a belt, in a pocket, or the like, and deliver insulin into the body via an infusion tube with a percutaneous needle or a cannula placed in the subcutaneous tissue.

Continuous insulin infusion provides greater control of a diabetic's condition, and hence, control schemes are being developed that allow insulin infusion pumps to monitor and regulate a user's blood glucose level in a substantially continuous and autonomous manner, for example, overnight while the user is sleeping. Regulating blood glucose level is complicated by variations in the response time for the type of insulin being used along with each user's individual insulin response. Furthermore, a user's daily activities and experiences may cause that user's insulin response to vary throughout the course of a day or from one day to the next. Thus, it is desirable to account for the anticipated variations or fluctuations in the user's insulin response caused by the user's activities or other condition(s) experienced by the user. Existing approaches often involve a user manually adjusting settings on a temporary or as-needed basis. Accordingly, there is a need facilitate improved glucose control that reduces the likelihood of manual errors while also reducing patient workload.

BRIEF SUMMARY

Medical devices and related systems and operating methods are provided. An embodiment of a method of automatically adjusting a control parameter for an operating mode of an infusion device involves monitoring a current operational context during autonomous operation of the infusion device to deliver fluid to a patient in accordance with the operating mode using an initial value for the control parameter, autonomously operating the infusion device to deliver the fluid to the patient in accordance with the operating mode using an adjusted value for the control parameter in lieu of the initial value in response to identifying the adjusted value for the control parameter associated with the current operational context, and thereafter reverting the control parameter to the initial value.

In another embodiment, a method of autonomously delivering fluid using an infusion device involves determining initial commands for delivering the fluid based at least in part on a difference between one or more measurement values of a physiological condition in a body of a patient and a normal target value for the physiological condition in the body of the patient, and in response to detecting a current operational context corresponds to an operational context previously associated with an anomalous state of the physiological condition of the patient, determining adjusted commands for delivering the fluid based at least in part on an updated difference between one or more subsequent measurement values of the physiological condition in the body of the patient and an adjusted target value for the physiological condition associated with the operational context in lieu of the normal target value and thereafter determining subsequent commands for delivering the fluid based at least in part on the normal target value.

In another embodiment, an infusion system is provided. The infusion system includes an actuation arrangement operable to deliver fluid to a patient, a data storage element to maintain associations between adjusted control parameter values and historical operational contexts for the patient, and a control system coupled to the actuation arrangement and the data storage element to monitor a current operational context during autonomous operation of the actuation arrangement to deliver the fluid to the patient in accordance with an operating mode using an initial value for a control parameter and in response to determining the current operational context matches a historical operational context of the historical operational contexts, temporarily determine commands for autonomously operating the actuation arrangement in accordance with the operating mode using a respective adjusted control parameter value associated with the historical operational context instead of the initial value.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

Figure 1:
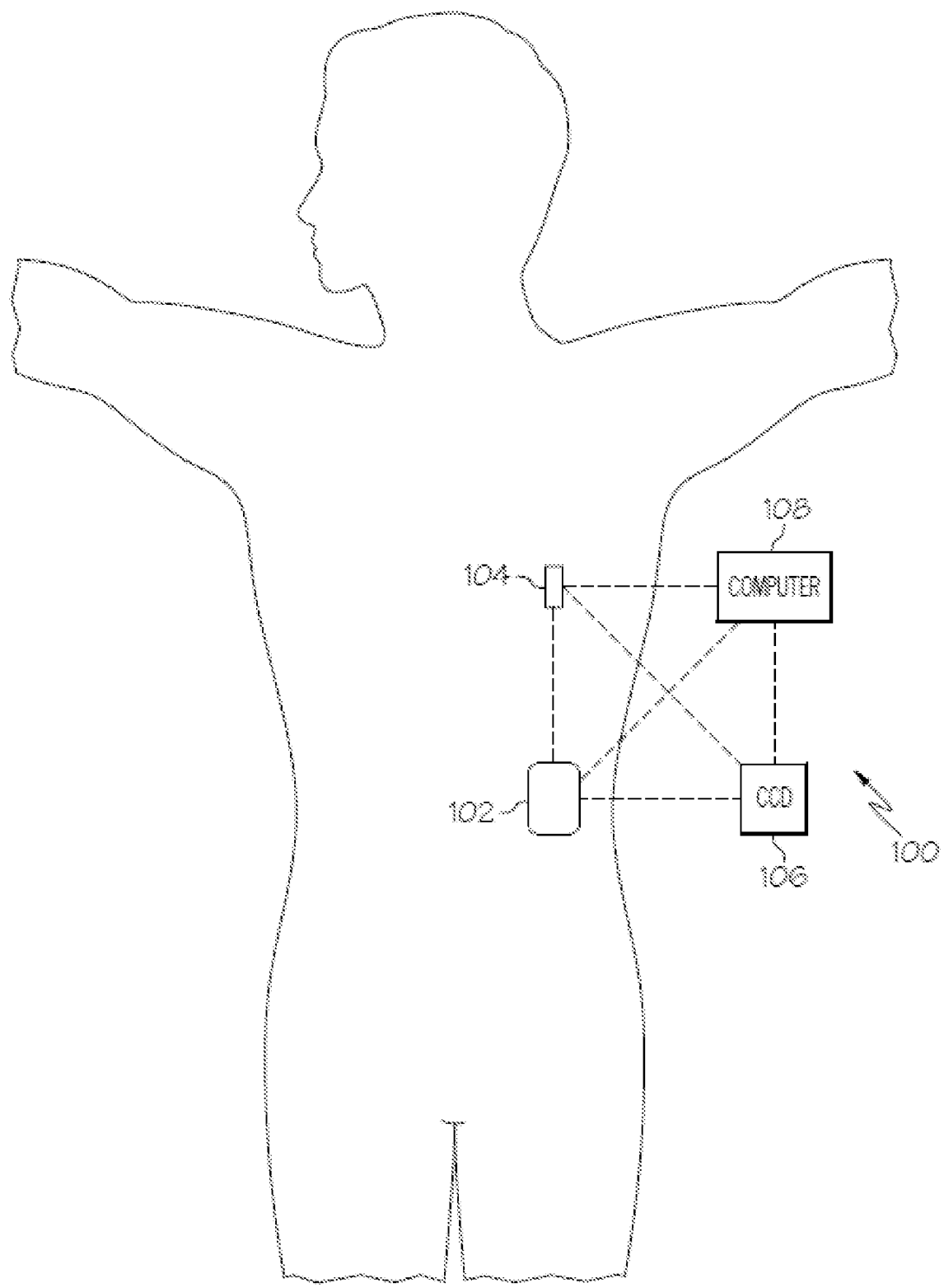
FIG. 1 depicts an exemplary embodiment of an infusion system.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Exemplary embodiments of the subject matter described herein are implemented in conjunction with medical devices, such as portable electronic medical devices. Although many different applications are possible, the following description focuses on embodiments that incorporate a fluid infusion device (or infusion pump) as part of an infusion system deployment. That said, the subject matter described herein is not limited to infusion devices (or any particular configuration or realization thereof) and may be implemented in an equivalent manner in the context of multiple daily injection (MDI) therapy regimen or other medical devices, such as continuous glucose monitoring (CGM) devices, injection pens (e.g., smart injection pens), and the like. For the sake of brevity, conventional techniques related to infusion system operation, insulin pump and/or infusion set operation, and other functional aspects of the systems (and the individual operating components of the systems) may not be described in detail here. Examples of infusion pumps may be of the type described in, but not limited to, U.S. Pat. Nos. 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893; each of which are herein incorporated by reference.

Generally, a fluid infusion device includes a motor or other actuation arrangement that is operable to displace a plunger (or stopper) or other delivery mechanism to deliver a dosage of fluid, such as insulin, from a reservoir provided within the fluid infusion device to the body of a patient. Dosage commands that govern operation of the motor may be generated in an automated manner in accordance with the delivery control scheme associated with a particular operating mode, and the dosage commands may be generated in a manner that is influenced by a current (or most recent) measurement of a physiological condition in the body of the user. For example, in a closed-loop operating mode, dosage commands may be generated based on a difference between a current (or most recent) measurement of the interstitial fluid glucose level in the body of the user and a target (or reference) glucose value. In this regard, the rate of infusion may vary as the difference between a current measurement value and the target measurement value fluctuates. For purposes of explanation, the subject matter is described herein in the context of the infused fluid being insulin for regulating a glucose level of a user (or patient); however, it should be appreciated that many other fluids may be administered through infusion, and the subject matter described herein is not necessarily limited to use with insulin. Additionally, for purposes of explanation, the subject matter may be described herein in the context of a diabetes patient management system that supports adjusting certain settings of an insulin infusion device used by a patient using a cloud-based architecture, wherein most of the processor-intensive tasks are performed by one or more server systems that communicate with other devices in the system, e.g., a mobile client device, a portable insulin infusion device, a source of data (such as patient-related data, insulin pump data, and the like), and possibly other remote devices.

Exemplary embodiments of the subject matter described herein generally relate to automatically adjusting control parameters utilized by operating modes of an infusion device, such as a control target or reference for a closed-loop operating mode, in a personalized manner based on the current or real-time operational context (e.g., the time of day, the day of the week, the location of the patient, the activity or behavior the patient is engaged in, and the like). For example, based on analysis of relationships between a patient's historical glucose measurement data during operation in a closed-loop operating mode and corresponding contextual data, a correlation between a particular operational context and an anomalous physiological state or condition of the patient, such as, for example, a high glucose (or hyperglycemic) event (e.g., a glucose level above a threshold), a low glucose (or hypoglycemic) event (e.g., a glucose level below a threshold), a glucose variability event or other glucose excursion event (e.g., a time in range below a threshold value), and/or the like. In this regard, an operational context that has been previously associated with recurrence of an anomalous state of the patient's physiological condition may be identified as a potentially problematic operational context for the patient.

As described in greater detail below, for a detected problematic operational context associated with a particular anomalous condition of the patient, an adjusted closed-loop control target may be identified that is likely to sufficiently mitigate the anomalous condition during autonomous operation concurrent with the potentially problematic operational context. Thereafter, in response to detecting that potentially problematic operational context in real-time, the closed-loop control system may be automatically altered or otherwise adjusted to temporarily utilize the adjusted closed-loop control target associated with that operational context for a limited duration of time before reverting to the original closed-loop control target, thereby reducing the likelihood of recurrence of the anomalous physiological state or condition during recurrence of that previously-problematic operational context without exiting the closed-loop operating mode and otherwise maintaining the operating mode or control scheme constant. It should be noted that the magnitude of the adjustment to the closed-loop control target may vary depending on the particular operational context and/or the magnitude of the adjustment may be personalized and/or optimized based on the patient's historical data associated with the operational context (e.g., using physiological simulations, cost functions, etc.). While the subject matter may be primarily discussed herein in the context of adjusting a closed-loop control target, the subject matter described herein is not limited to a closed-loop control scheme and may be implemented in an equivalent manner to adjust a control target or similar control parameter for other control schemes or systems (e.g., open-loop modes, semi-closed-loop modes, and the like). For example, an open-loop basal rate may be automatically altered or otherwise adjusted to temporarily to reducing the likelihood of an anomalous physiological state or condition during a particular operational context.

In one or more embodiments, a number of different adjusted closed-loop control targets are identified, and for each adjusted closed-loop control target, a corresponding simulated glucose profile may be determined using the adjusted closed-loop control target in conjunction with the patient's event log data (e.g., meal data, exercise data, sleep data, bolus data, and/or the like) corresponding to the preceding operation during the detected operational context in the closed-loop operating mode. Thereafter, the simulated glucose profiles may be analyzed to identify or otherwise select an optimal closed-loop control target to be utilized. For example, in one embodiment, the adjusted closed-loop control target value that maximizes a time in range (e.g., the amount of time spent within a predefined range of glucose values) or a cumulative amount of time within some threshold of the normal closed-loop control target may be selected as the optimal closed-loop control target value to be associated with the detected operational context, while in other embodiments, the adjusted closed-loop control target value that minimizes the probability of recurrence of the anomalous physiological state or condition may be selected as the optimal closed-loop control target value to be associated with the detected operational context. In this regard, it should be noted that there are numerous different manners to identify or otherwise select an optimal value for a variable, and the subject matter described herein is not intended to be limited to any particular manner for identifying the adjusted closed-loop control target value to be utilized. For example, in some embodiments, one or more cost functions may be applied to each of the simulated glucose profiles to determine a respective cost associated with each respective adjusted closed-loop control target value, which, in turn is utilized to identify an optimized adjusted closed-loop control target that achieves the minimum cost.

Infusion System Overview

FIG. 1 depicts one exemplary embodiment of an infusion system 100 that includes, without limitation, a fluid infusion device (or infusion pump) 102, a sensing arrangement 104, a command control device (CCD) 106, and a computer 108. The components of an infusion system 100 may be realized using different platforms, designs, and configurations, and the embodiment shown in FIG. 1 is not exhaustive or limiting. In practice, the infusion device 102 and the sensing arrangement 104 are secured at desired locations on the body of a user (or patient), as illustrated in FIG. 1. In this regard, the locations at which the infusion device 102 and the sensing arrangement 104 are secured to the body of the user in FIG. 1 are provided only as a representative, non-limiting, example. The elements of the infusion system 100 may be similar to those described in U.S. Pat. No. 8,674,288, the subject matter of which is hereby incorporated by reference in its entirety.

In the illustrated embodiment of FIG. 1, the infusion device 102 is designed as a portable medical device suitable for infusing a fluid, a liquid, a gel, or other medicament into the body of a user. In exemplary embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. In some embodiments, the fluid may include a nutritional supplement, a dye, a tracing medium, a saline medium, a hydration medium, or the like.

The sensing arrangement 104 generally represents the components of the infusion system 100 configured to sense, detect, measure or otherwise quantify a condition of the user, and may include a sensor, a monitor, or the like, for providing data indicative of the condition that is sensed, detected, measured or otherwise monitored by the sensing arrangement. In this regard, the sensing arrangement 104 may include electronics and enzymes reactive to a biological condition, such as a blood glucose level, or the like, of the user, and provide data indicative of the blood glucose level to the infusion device 102, the CCD 106 and/or the computer 108. For example, the infusion device 102, the CCD 106 and/or the computer 108 may include a display for presenting information or data to the user based on the sensor data received from the sensing arrangement 104, such as, for example, a current glucose level of the user, a graph or chart of the user's glucose level versus time, device status indicators, alert messages, or the like. In other embodiments, the infusion device 102, the CCD 106 and/or the computer 108 may include electronics and software that are configured to analyze sensor data and operate the infusion device 102 to deliver fluid to the body of the user based on the sensor data and/or preprogrammed delivery routines. Thus, in exemplary embodiments, one or more of the infusion device 102, the sensing arrangement 104, the CCD 106, and/or the computer 108 includes a transmitter, a receiver, and/or other transceiver electronics that allow for communication with other components of the infusion system 100, so that the sensing arrangement 104 may transmit sensor data or monitor data to one or more of the infusion device 102, the CCD 106 and/or the computer 108.

Still referring to FIG. 1, in various embodiments, the sensing arrangement 104 may be secured to the body of the user or embedded in the body of the user at a location that is remote from the location at which the infusion device 102 is secured to the body of the user. In various other embodiments, the sensing arrangement 104 may be incorporated within the infusion device 102. In other embodiments, the sensing arrangement 104 may be separate and apart from the infusion device 102, and may be, for example, part of the CCD 106. In such embodiments, the sensing arrangement 104 may be configured to receive a biological sample, analyte, or the like, to measure a condition of the user.

In some embodiments, the CCD 106 and/or the computer 108 may include electronics and other components configured to perform processing, delivery routine storage, and to control the infusion device 102 in a manner that is influenced by sensor data measured by and/or received from the sensing arrangement 104. By including control functions in the CCD 106 and/or the computer 108, the infusion device 102 may be made with more simplified electronics. However, in other embodiments, the infusion device 102 may include all control functions, and may operate without the CCD 106 and/or the computer 108. In various embodiments, the CCD 106 may be a portable electronic device. In addition, in various embodiments, the infusion device 102 and/or the sensing arrangement 104 may be configured to transmit data to the CCD 106 and/or the computer 108 for display or processing of the data by the CCD 106 and/or the computer 108.

In some embodiments, the CCD 106 and/or the computer 108 may provide information to the user that facilitates the user's subsequent use of the infusion device 102. For example, the CCD 106 may provide information to the user to allow the user to determine the rate or dose of medication to be administered into the user's body. In other embodiments, the CCD 106 may provide information to the infusion device 102 to autonomously control the rate or dose of medication administered into the body of the user. In some embodiments, the sensing arrangement 104 may be integrated into the CCD 106. Such embodiments may allow the user to monitor a condition by providing, for example, a sample of his or her blood to the sensing arrangement 104 to assess his or her condition. In some embodiments, the sensing arrangement 104 and the CCD 106 may be used for determining glucose levels in the blood and/or body fluids of the user without the use of, or necessity of, a wire or cable connection between the infusion device 102 and the sensing arrangement 104 and/or the CCD 106.

In some embodiments, the sensing arrangement 104 and/or the infusion device 102 are cooperatively configured to utilize a closed-loop system for delivering fluid to the user. Examples of sensing devices and/or infusion pumps utilizing closed-loop systems may be found at, but are not limited to, the following U.S. Pat. Nos. 6,088,608, 6,119,028, 6,589,229, 6,740,072, 6,827,702, 7,323,142, and 7,402,153 or United States Patent Application Publication No. 2014/0066889, all of which are incorporated herein by reference in their entirety. In such embodiments, the sensing arrangement 104 is configured to sense or measure a condition of the user, such as, blood glucose level or the like. The infusion device 102 is configured to deliver fluid in response to the condition sensed by the sensing arrangement 104. In turn, the sensing arrangement 104 continues to sense or otherwise quantify a current condition of the user, thereby allowing the infusion device 102 to deliver fluid continuously in response to the condition currently (or most recently) sensed by the sensing arrangement 104 indefinitely. In some embodiments, the sensing arrangement 104 and/or the infusion device 102 may be configured to utilize the closed-loop system only for a portion of the day, for example only when the user is asleep or awake.

Figure 2:
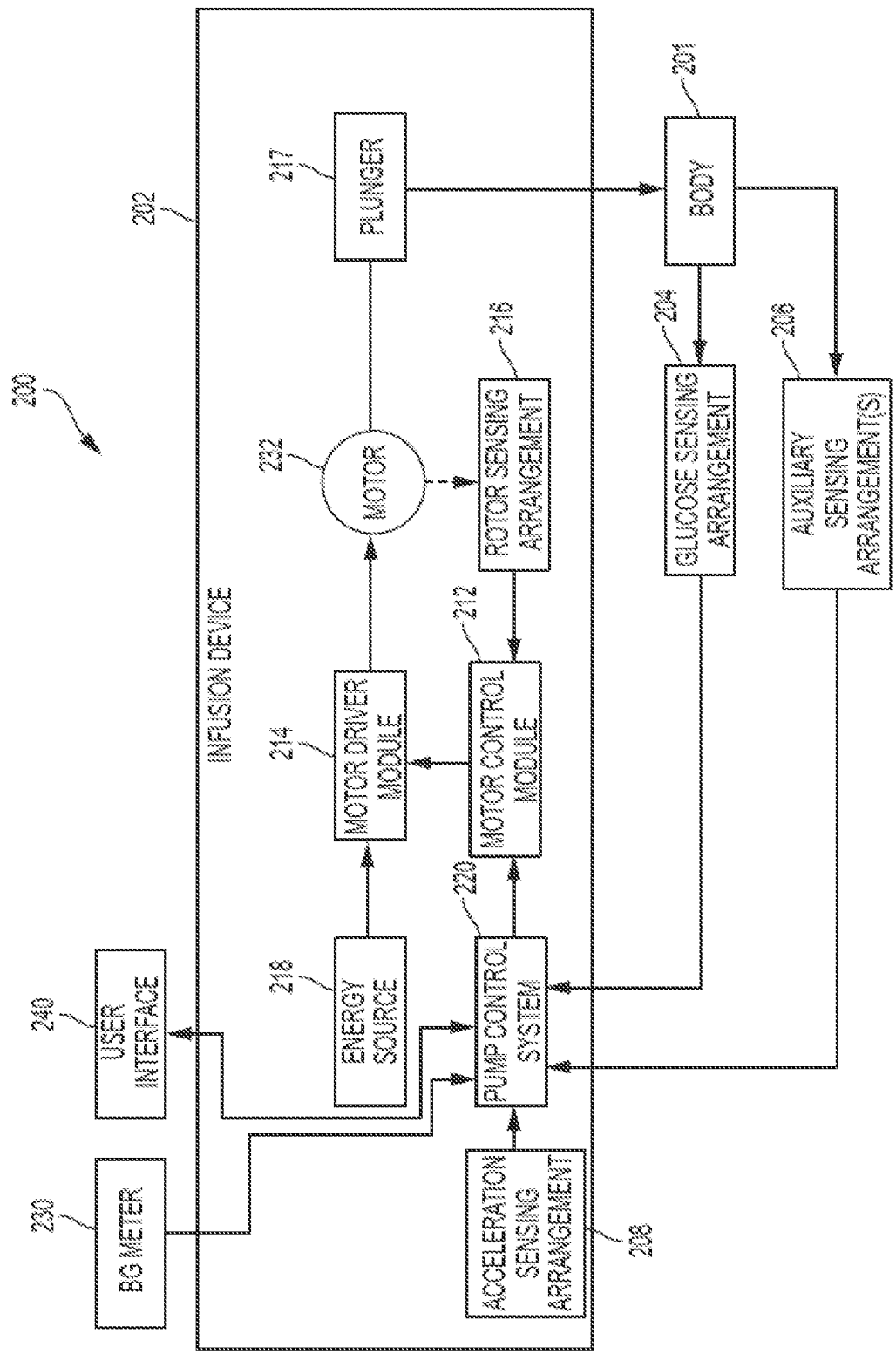
FIG. 2 is a block diagram of an exemplary control system suitable for use with a fluid infusion device in one or more embodiments.

FIG. 2 depicts an exemplary embodiment of a control system 200 suitable for use with an infusion device 202, such as the infusion device 102 described above. The control system 200 is capable of controlling or otherwise regulating a physiological condition in the body 201 of a patient to a desired (or target) value or otherwise maintain the condition within a range of acceptable values in an automated or autonomous manner. In one or more exemplary embodiments, the condition being regulated is sensed, detected, measured or otherwise quantified by a sensing arrangement 204 (e.g., sensing arrangement 104) communicatively coupled to the infusion device 202. However, it should be noted that in alternative embodiments, the condition being regulated by the control system 200 may be correlative to the measured values obtained by the sensing arrangement 204. That said, for clarity and purposes of explanation, the subject matter may be described herein in the context of the sensing arrangement 204 being realized as a glucose sensing arrangement that senses, detects, measures or otherwise quantifies the patient's glucose level, which is being regulated in the body 201 of the patient by the control system 200.

In exemplary embodiments, the sensing arrangement 204 includes one or more interstitial glucose sensing elements that generate or otherwise output electrical signals (alternatively referred to herein as measurement signals) having a signal characteristic that is correlative to, influenced by, or otherwise indicative of the relative interstitial fluid glucose level in the body 201 of the patient. The output electrical signals are filtered or otherwise processed to obtain a measurement value indicative of the patient's interstitial fluid glucose level. In exemplary embodiments, a blood glucose meter 230, such as a finger stick device, is utilized to directly sense, detect, measure or otherwise quantify the blood glucose in the body 201 of the patient. In this regard, the blood glucose meter 230 outputs or otherwise provides a measured blood glucose value that may be utilized as a reference measurement for calibrating the sensing arrangement 204 and converting a measurement value indicative of the patient's interstitial fluid glucose level into a corresponding calibrated blood glucose value. For purposes of explanation, the calibrated glucose value calculated based on the electrical signals output by the sensing element(s) of the sensing arrangement 204 may alternatively be referred to herein as the sensor glucose value, the sensed glucose value, or variants thereof.

In the illustrated embodiment, the control system 200 also includes one or more additional sensing arrangements 206, 208 configured to sense, detect, measure or otherwise quantify a characteristic of the body 201 of the patient that is indicative of a condition in the body 201 of the patient. In this regard, in addition to the glucose sensing arrangement 204, one or more auxiliary sensing arrangements 206 may be worn, carried, or otherwise associated with the body 201 of the patient to measure characteristics or conditions of the patient (or the patient's activity) that may influence the patient's glucose levels or insulin sensitivity. For example, a heart rate sensing arrangement 206 could be worn on or otherwise associated with the patient's body 201 to sense, detect, measure or otherwise quantify the patient's heart rate, which, in turn, may be indicative of exercise (and the intensity thereof) that is likely to influence the patient's glucose levels or insulin response in the body 201. In yet another embodiment, another invasive, interstitial, or subcutaneous sensing arrangement 206 may be inserted into the body 201 of the patient to obtain measurements of another physiological condition that may be indicative of exercise (and the intensity thereof), such as, for example, a lactate sensor, a ketone sensor, or the like. Depending on the embodiment, the auxiliary sensing arrangement(s) 206 could be realized as a standalone component worn by the patient, or alternatively, the auxiliary sensing arrangement(s) 206 may be integrated with the infusion device 202 or the glucose sensing arrangement 204.

The illustrated control system 200 also includes an acceleration sensing arrangement 208 (or accelerometer) that may be worn on or otherwise associated with the patient's body 201 to sense, detect, measure or otherwise quantify an acceleration of the patient's body 201, which, in turn, may be indicative of exercise or some other condition in the body 201 that is likely to influence the patient's insulin response. While the acceleration sensing arrangement 208 is depicted as being integrated into the infusion device 202 in FIG. 2, in alternative embodiments, the acceleration sensing arrangement 208 may be integrated with another sensing arrangement 204, 206 on the body 201 of the patient, or the acceleration sensing arrangement 208 may be realized as a separate standalone component that is worn by the patient.

In some embodiments, the infusion device 202 (or the control system 200) may also include one or more environmental sensing arrangements to sense, detect, measure or otherwise quantify the current operating environment around the infusion device 202. In this regard, the environmental sensing arrangements may include one or more of a temperature sensing arrangement (or thermometer), a humidity sensing arrangement, a pressure sensing arrangement (or barometer), and/or the like. Additionally, the infusion device 202 (or the control system 200) may also include a position sensing arrangement to sense, detect, measure or otherwise quantify the current geographic location of the infusion device 202, such as, for example, a global positioning system (GPS) receiver. Again, it should be noted that such sensing arrangements could be integrated into the infusion device 202, integrated with other components, or realized as a separate standalone components that are worn or carried by the patient.

In the illustrated embodiment, the pump control system 220 generally represents the electronics and other components of the infusion device 202 that control operation of the fluid infusion device 202 according to a desired infusion delivery program in a manner that is influenced by the sensed glucose value indicating the current glucose level in the body 201 of the patient. For example, to support a closed-loop operating mode, the pump control system 220 maintains, receives, or otherwise obtains a target or commanded glucose value, and automatically generates or otherwise determines dosage commands for operating an actuation arrangement, such as a motor 232, to displace the plunger 217 and deliver insulin to the body 201 of the patient based on the difference between the sensed glucose value and the target glucose value. In other operating modes, the pump control system 220 may generate or otherwise determine dosage commands configured to maintain the sensed glucose value below an upper glucose limit, above a lower glucose limit, or otherwise within a desired range of glucose values. In practice, the infusion device 202 may store or otherwise maintain the target value, upper and/or lower glucose limit(s), insulin delivery limit(s), and/or other glucose threshold value(s) in a data storage element accessible to the pump control system 220. In one or more exemplary embodiments, the pump control system 220 automatically adjusts or adapts one or more parameters or other control information used to generate commands for operating the motor 232 in a manner that accounts for a likely change in the patient's glucose level or insulin response resulting from a meal, exercise, or other activity.

Still referring to FIG. 2, the target glucose value and other threshold glucose values utilized by the pump control system 220 may be received from an external component (e.g., CCD 106 and/or computing device 108) or be input by a patient via a user interface element 240 associated with the infusion device 202. In practice, the one or more user interface element(s) 240 associated with the infusion device 202 typically include at least one input user interface element, such as, for example, a button, a keypad, a keyboard, a knob, a joystick, a mouse, a touch panel, a touchscreen, a microphone or another audio input device, and/or the like. Additionally, the one or more user interface element(s) 240 include at least one output user interface element, such as, for example, a display element (e.g., a light-emitting diode or the like), a display device (e.g., a liquid crystal display or the like), a speaker or another audio output device, a haptic feedback device, or the like, for providing notifications or other information to the patient. It should be noted that although FIG. 2 depicts the user interface element(s) 240 as being separate from the infusion device 202, in practice, one or more of the user interface element(s) 240 may be integrated with the infusion device 202. Furthermore, in some embodiments, one or more user interface element(s) 240 are integrated with the sensing arrangement 204 in addition to and/or in alternative to the user interface element(s) 240 integrated with the infusion device 202. The user interface element(s) 240 may be manipulated by the patient to operate the infusion device 202 to deliver correction boluses, adjust target and/or threshold values, modify the delivery control scheme or operating mode, and the like, as desired.

Still referring to FIG. 2, in the illustrated embodiment, the infusion device 202 includes a motor control module 212 coupled to a motor 232 that is operable to displace a plunger 217 in a reservoir and provide a desired amount of fluid to the body 201 of a patient. In this regard, displacement of the plunger 217 results in the delivery of a fluid, such as insulin, that is capable of influencing the patient's physiological condition to the body 201 of the patient via a fluid delivery path (e.g., via tubing of an infusion set). A motor driver module 214 is coupled between an energy source 218 and the motor 232. The motor control module 212 is coupled to the motor driver module 214, and the motor control module 212 generates or otherwise provides command signals that operate the motor driver module 214 to provide current (or power) from the energy source 218 to the motor 232 to displace the plunger 217 in response to receiving, from a pump control system 220, a dosage command indicative of the desired amount of fluid to be delivered.

In exemplary embodiments, the energy source 218 is realized as a battery housed within the infusion device 202 that provides direct current (DC) power. In this regard, the motor driver module 214 generally represents the combination of circuitry, hardware and/or other electrical components configured to convert or otherwise transfer DC power provided by the energy source 218 into alternating electrical signals applied to respective phases of the stator windings of the motor 232 that result in current flowing through the stator windings that generates a stator magnetic field and causes the rotor of the motor 232 to rotate. The motor control module 212 is configured to receive or otherwise obtain a commanded dosage from the pump control system 220, convert the commanded dosage to a commanded translational displacement of the plunger 217, and command, signal, or otherwise operate the motor driver module 214 to cause the rotor of the motor 232 to rotate by an amount that produces the commanded translational displacement of the plunger 217. For example, the motor control module 212 may determine an amount of rotation of the rotor required to produce translational displacement of the plunger 217 that achieves the commanded dosage received from the pump control system 220. Based on the current rotational position (or orientation) of the rotor with respect to the stator that is indicated by the output of the rotor sensing arrangement 216, the motor control module 212 determines the appropriate sequence of alternating electrical signals to be applied to the respective phases of the stator windings that should rotate the rotor by the determined amount of rotation from its current position (or orientation). In embodiments where the motor 232 is realized as a BLDC motor, the alternating electrical signals commutate the respective phases of the stator windings at the appropriate orientation of the rotor magnetic poles with respect to the stator and in the appropriate order to provide a rotating stator magnetic field that rotates the rotor in the desired direction. Thereafter, the motor control module 212 operates the motor driver module 214 to apply the determined alternating electrical signals (e.g., the command signals) to the stator windings of the motor 232 to achieve the desired delivery of fluid to the patient.

When the motor control module 212 is operating the motor driver module 214, current flows from the energy source 218 through the stator windings of the motor 232 to produce a stator magnetic field that interacts with the rotor magnetic field. In some embodiments, after the motor control module 212 operates the motor driver module 214 and/or motor 232 to achieve the commanded dosage, the motor control module 212 ceases operating the motor driver module 214 and/or motor 232 until a subsequent dosage command is received. In this regard, the motor driver module 214 and the motor 232 enter an idle state during which the motor driver module 214 effectively disconnects or isolates the stator windings of the motor 232 from the energy source 218. In other words, current does not flow from the energy source 218 through the stator windings of the motor 232 when the motor 232 is idle, and thus, the motor 232 does not consume power from the energy source 218 in the idle state, thereby improving efficiency.

Depending on the embodiment, the motor control module 212 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In exemplary embodiments, the motor control module 212 includes or otherwise accesses a data storage element or memory, including any sort of random access memory (RAM), read only memory (ROM), flash memory, registers, hard disks, removable disks, magnetic or optical mass storage, or any other short or long term storage media or other non-transitory computer-readable medium, which is capable of storing programming instructions for execution by the motor control module 212. The computer-executable programming instructions, when read and executed by the motor control module 212, cause the motor control module 212 to perform or otherwise support the tasks, operations, functions, and processes described herein.

It should be appreciated that FIG. 2 is a simplified representation of the infusion device 202 for purposes of explanation and is not intended to limit the subject matter described herein in any way. In this regard, depending on the embodiment, some features and/or functionality of the sensing arrangement 204 may implemented by or otherwise integrated into the pump control system 220, or vice versa. Similarly, in practice, the features and/or functionality of the motor control module 212 may be implemented by or otherwise integrated into the pump control system 220, or vice versa. Furthermore, the features and/or functionality of the pump control system 220 may be implemented by control electronics located in the fluid infusion device 202, while in alternative embodiments, the pump control system 220 may be implemented by a remote computing device that is physically distinct and/or separate from the infusion device 202, such as, for example, the CCD 106 or the computing device 108.

Figure 3:
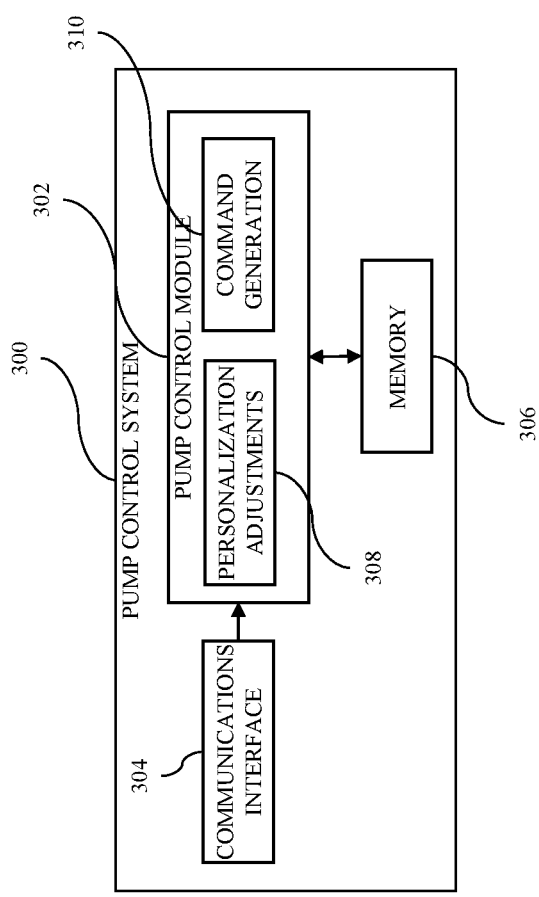
FIG. 3 is a block diagram of an exemplary pump control system suitable for use in the infusion device in the control system of FIG. 2 in one or more embodiments.

FIG. 3 depicts an exemplary embodiment of a pump control system 300 suitable for use as the pump control system 220 in FIG. 2 in accordance with one or more embodiments. The illustrated pump control system 300 includes, without limitation, a pump control module 302, a communications interface 304, and a data storage element (or memory) 306. The pump control module 302 is coupled to the communications interface 304 and the memory 306, and the pump control module 302 is suitably configured to support the operations, tasks, and/or processes described herein. In various embodiments, the pump control module 302 is also coupled to one or more user interface elements (e.g., user interface 240) for receiving user inputs (e.g., target glucose values or other glucose thresholds) and providing notifications, alerts, or other therapy information to the patient.

The communications interface 304 generally represents the hardware, circuitry, logic, firmware and/or other components of the pump control system 300 that are coupled to the pump control module 302 and configured to support communications between the pump control system 300 and the various sensing arrangements 204, 206, 208. In this regard, the communications interface 304 may include or otherwise be coupled to one or more transceiver modules capable of supporting wireless communications between the pump control system 220, 300 and the sensing arrangement(s) 204, 206, 208. For example, the communications interface 304 may be utilized to receive sensor measurement values or other measurement data from each sensing arrangement 204, 206, 208 in a control system 200. In other embodiments, the communications interface 304 may be configured to support wired communications to/from the sensing arrangement(s) 204, 206, 208. In various embodiments, the communications interface 304 may also support communications with another electronic device (e.g., CCD 106 and/or computer 108) in an infusion system (e.g., to upload sensor measurement values to a server or other computing device, receive control information from a server or other computing device, and the like).

The pump control module 302 generally represents the hardware, circuitry, logic, firmware and/or other component of the pump control system 300 that is coupled to the communications interface 304 and configured to determine dosage commands for operating the motor 232 to deliver fluid to the body 201 based on measurement data received from the sensing arrangements 204, 206, 208 and perform various additional tasks, operations, functions and/or operations described herein. For example, in exemplary embodiments, pump control module 302 implements or otherwise executes a command generation application 310 that supports one or more autonomous operating modes and calculates or otherwise determines dosage commands for operating the motor 232 of the infusion device 202 in an autonomous operating mode based at least in part on a current measurement value for a condition in the body 201 of the patient. For example, in a closed-loop operating mode, the command generation application 310 may determine a dosage command for operating the motor 232 to deliver insulin to the body 201 of the patient based at least in part on the current glucose measurement value most recently received from the sensing arrangement 204 to regulate the patient's blood glucose level to a target reference glucose value. Additionally, the command generation application 310 may generate dosage commands for boluses that are manually-initiated or otherwise instructed by a patient via a user interface element.

In exemplary embodiments, the pump control module 302 also implements or otherwise executes a personalization application 308 that is cooperatively configured to interact with the command generation application 310 to support adjusting dosage commands or control information dictating the manner in which dosage commands are generated in a personalized, patient-specific manner. In this regard, in some embodiments, based on correlations between current or recent measurement data and the current operational context relative to historical data associated with the patient, the personalization application 308 may adjust or otherwise modify values for one or more parameters utilized by the command generation application 310 when determining dosage commands, for example, by modifying a parameter value at a register or location in memory 306 referenced by the command generation application 310. In yet other embodiments, the personalization application 308 may predict meals or other events or activities that are likely to be engaged in by the patient and output or otherwise provide an indication of the predicted patient behavior, which, in turn, may then be utilized to adjust the manner in which dosage commands are generated to regulate glucose in a manner that accounts for the patient's predicted behavior in a personalized manner. In some embodiments, the personalization application 308 may support automatically performing personalized adjustments of control parameters utilized by the command generation application 310.

Still referring to FIG. 3, depending on the embodiment, the pump control module 302 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In this regard, the steps of a method or algorithm described in connection with the embodiments disclosed herein may be embodied directly in hardware, in firmware, in a software module executed by the pump control module 302, or in any practical combination thereof. In exemplary embodiments, the pump control module 302 includes or otherwise accesses the data storage element or memory 306, which may be realized using any sort of non-transitory computer-readable medium capable of storing programming instructions for execution by the pump control module 302. The computer-executable programming instructions, when read and executed by the pump control module 302, cause the pump control module 302 to implement or otherwise generate the applications 308, 310 and perform tasks, operations, functions, and processes described herein.

It should be understood that FIG. 3 is a simplified representation of a pump control system 300 for purposes of explanation and is not intended to limit the subject matter described herein in any way. For example, in some embodiments, the features and/or functionality of the motor control module 212 may be implemented by or otherwise integrated into the pump control system 300 and/or the pump control module 302, for example, by the command generation application 310 converting the dosage command into a corresponding motor command, in which case, the separate motor control module 212 may be absent from an embodiment of the infusion device 202.

Figure 4:
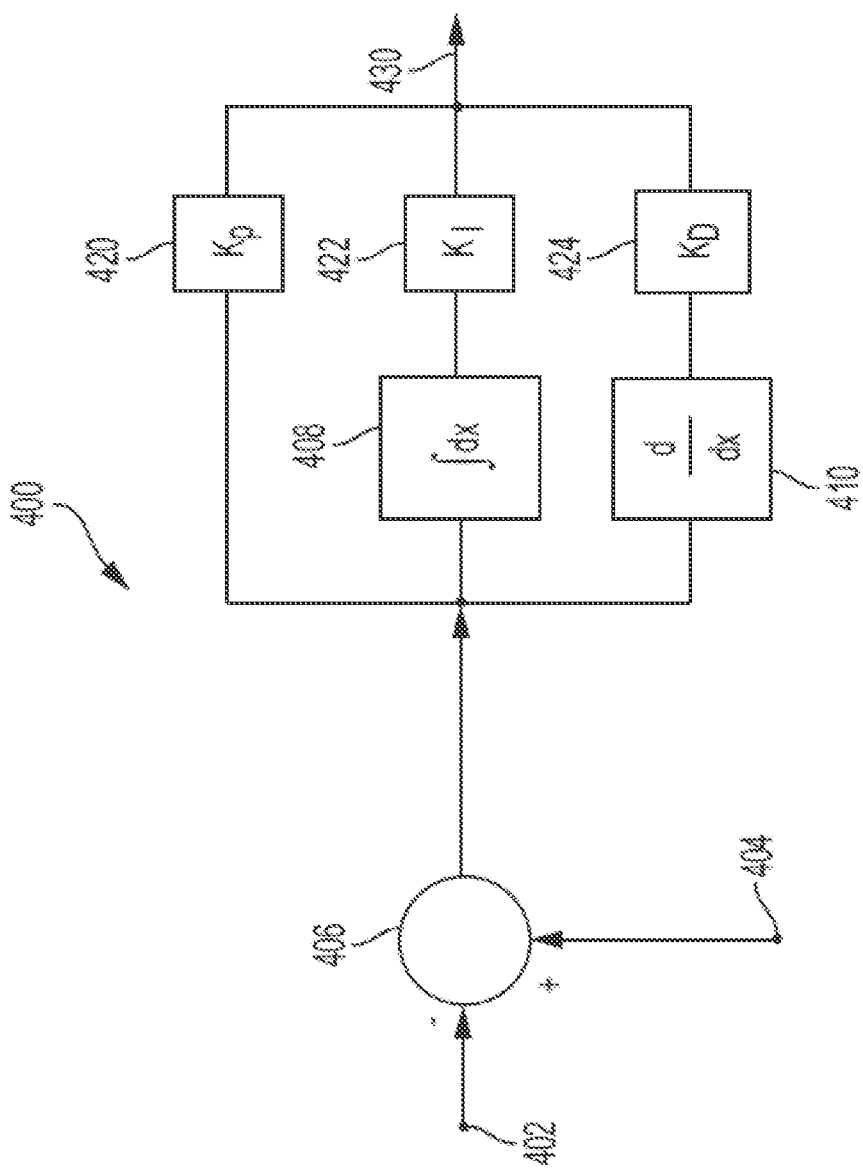
FIG. 4 is a block diagram of a closed-loop control system that may be implemented or otherwise supported by the pump control system in the fluid infusion device of FIGS. 2-3 in one or more exemplary embodiments.

FIG. 4 depicts an exemplary closed-loop control system 400 that may be implemented by a pump control system 220, 300 to provide a closed-loop operating mode that autonomously regulates a condition in the body of a patient to a reference (or target) value. It should be appreciated that FIG. 4 is a simplified representation of the control system 400 for purposes of explanation and is not intended to limit the subject matter described herein in any way.

In exemplary embodiments, the control system 400 receives or otherwise obtains a target glucose value at input 402. In some embodiments, the target glucose value may be stored or otherwise maintained by the infusion device 202 (e.g., in memory 306), however, in some alternative embodiments, the target value may be received from an external component (e.g., CCD 106 and/or computer 108). In one or more embodiments, the target glucose value may be calculated or otherwise determined prior to entering the closed-loop operating mode based on one or more patient-specific control parameters. For example, the target blood glucose value may be calculated based at least in part on a patient-specific reference basal rate and a patient-specific daily insulin requirement, which are determined based on historical delivery information over a preceding interval of time (e.g., the amount of insulin delivered over the preceding 24 hours). The control system 400 also receives or otherwise obtains a current glucose measurement value (e.g., the most recently obtained sensor glucose value) from the sensing arrangement 204 at input 404. The illustrated control system 400 implements or otherwise provides proportional-integral-derivative (PID) control to determine or otherwise generate delivery commands for operating the motor 232 based at least in part on the difference between the target glucose value and the current glucose measurement value. In this regard, the PID control attempts to minimize the difference between the measured value and the target value, and thereby regulates the measured value to the desired value. PID control parameters are applied to the difference between the target glucose level at input 402 and the measured glucose level at input 404 to generate or otherwise determine a dosage (or delivery) command provided at output 430. Based on that delivery command, the motor control module 212 operates the motor 232 to deliver insulin to the body of the patient to influence the patient's glucose level, and thereby reduce the difference between a subsequently measured glucose level and the target glucose level.

The illustrated control system 400 includes or otherwise implements a summation block 406 configured to determine a difference between the target value obtained at input 402 and the measured value obtained from the sensing arrangement 204 at input 404, for example, by subtracting the target value from the measured value. The output of the summation block 406 represents the difference between the measured and target values, which is then provided to each of a proportional term path, an integral term path, and a derivative term path. The proportional term path includes a gain block 420 that multiplies the difference by a proportional gain coefficient, $K_P$, to obtain the proportional term. The integral term path includes an integration block 408 that integrates the difference and a gain block 422 that multiplies the integrated difference by an integral gain coefficient, $K_I$, to obtain the integral term. The derivative term path includes a derivative block 410 that determines the derivative of the difference and a gain block 424 that multiplies the derivative of the difference by a derivative gain coefficient, $K_D$, to obtain the derivative term. The proportional term, the integral term, and the derivative term are then added or otherwise combined to obtain a delivery command that is utilized to operate the motor at output 430. Various implementation details pertaining to closed-loop PID control and determining gain coefficients are described in greater detail in U.S. Pat. No. 7,402,153, which is incorporated by reference.

In one or more exemplary embodiments, the PID gain coefficients are patient-specific and dynamically calculated or otherwise determined prior to entering the closed-loop operating mode based on historical insulin delivery information (e.g., amounts and/or timings of previous dosages, historical correction bolus information, or the like), historical sensor measurement values, historical reference blood glucose measurement values, user-reported or user-input events (e.g., meals, exercise, and the like), and the like. In this regard, one or more patient-specific control parameters (e.g., an insulin sensitivity factor, a daily insulin requirement, an insulin limit, a reference basal rate, a reference fasting glucose, an active insulin action duration, pharmodynamical time constants, or the like) may be utilized to compensate, correct, or otherwise adjust the PID gain coefficients to account for various operating conditions experienced and/or exhibited by the infusion device 202. The PID gain coefficients may be maintained by the memory 306 accessible to the pump control module 302. In this regard, the memory 306 may include a plurality of registers associated with the control parameters for the PID control. For example, a first parameter register may store the target glucose value and be accessed by or otherwise coupled to the summation block 406 at input 402, and similarly, a second parameter register accessed by the proportional gain block 420 may store the proportional gain coefficient, a third parameter register accessed by the integration gain block 422 may store the integration gain coefficient, and a fourth parameter register accessed by the derivative gain block 424 may store the derivative gain coefficient.

As described in greater detail below in the context of FIGS. 6-7, in exemplary embodiments, the closed-loop control target value at the input 402 is temporarily adjusted automatically in response to detecting an operational context that is correlated to an anomalous glycemic condition or event for the patient. For example, during an operational context (e.g., a particular time of day on a particular day of the week) that is correlative to the patient exhibiting a hypoglycemic event, an adjusted closed-loop control target value may be utilized at the input 402 that is greater than the normal (or preceding) control target value previously utilized at the input 402 to temporarily decrease the rate or amount of insulin infused in response to detecting that operational context. Thus, during a particular time of day on a particular day of the week where the patient is prone or otherwise susceptible to experiencing hypoglycemia, the closed-loop control target value at the input 402 is automatically adjusted in real-time to reduce the likelihood of the patient experience hypoglycemia for a temporary duration of time at or around that particular time of day on that particular day of the week. After the period of time during which the patient has previously exhibited hypoglycemia has elapsed, the closed-loop control target value at the input 402 may automatically revert to the normal (or preceding) target value (e.g., the original target value that was input or set by the patient, determined based on the patient's historical delivery information, or the like). Conversely, in response to detecting an operational context that is correlative to a hyperglycemic event, an adjusted closed-loop control target value may be utilized at the input 402 that is less than the normal (or preceding) control target value utilized at the input 402 to temporarily increase the rate or amount of insulin infused in response to detecting that operational context, thereby reducing the likelihood of the patient experiencing hyperglycemia.

Figure 5:
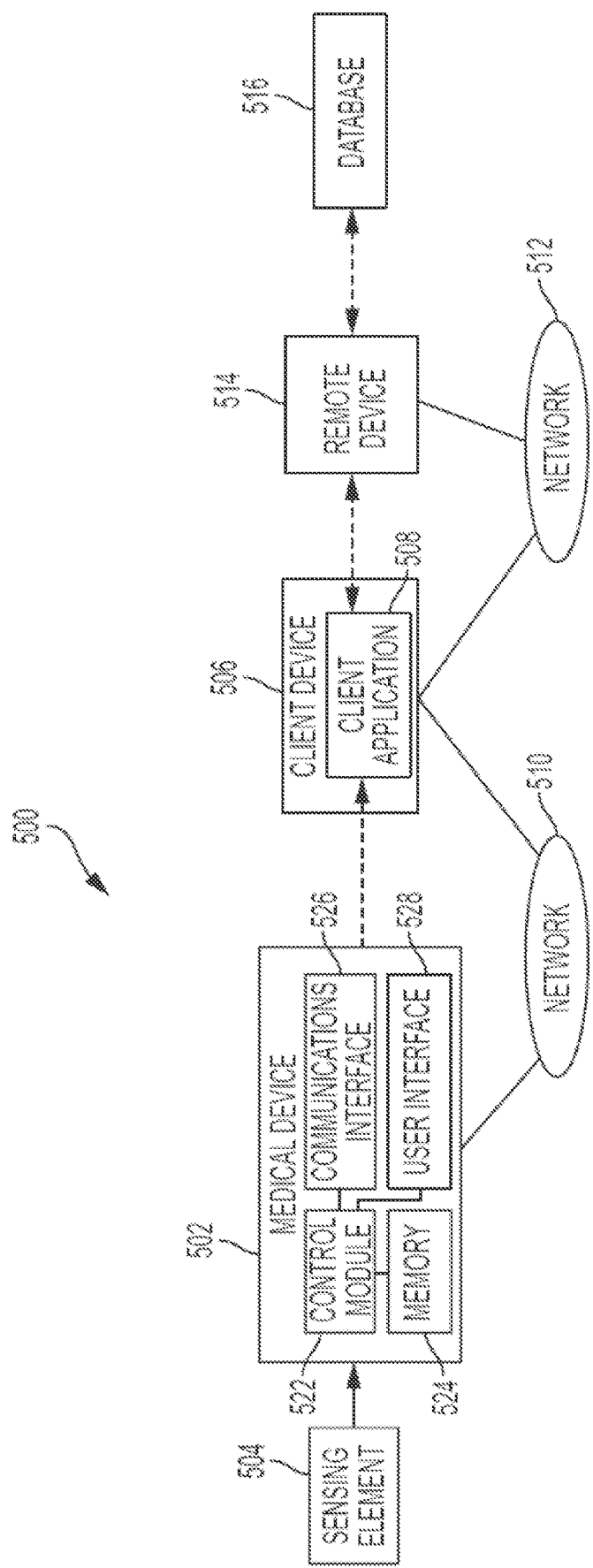
FIG. 5 is a block diagram of an exemplary patient monitoring system.

FIG. 5 depicts an exemplary embodiment of a patient monitoring system 500. The patient monitoring system 500 includes a medical device 502 that is communicatively coupled to a sensing element 504 that is inserted into the body of a patient or otherwise worn by the patient to obtain measurement data indicative of a physiological condition in the body of the patient, such as a sensed glucose level. The medical device 502 is communicatively coupled to a client device 506 via a communications network 510, with the client device 506 being communicatively coupled to a remote device 514 via another communications network 512. In this regard, the client device 506 may function as an intermediary for uploading or otherwise providing measurement data from the medical device 502 to the remote device 514. It should be appreciated that FIG. 5 depicts a simplified representation of a patient monitoring system 500 for purposes of explanation and is not intended to limit the subject matter described herein in any way.

In exemplary embodiments, the client device 506 is realized as a mobile phone, a smartphone, a tablet computer, or other similar mobile electronic device; however, in other embodiments, the client device 506 may be realized as any sort of electronic device capable of communicating with the medical device 502 via network 510, such as a laptop or notebook computer, a desktop computer, or the like. In exemplary embodiments, the network 510 is realized as a Bluetooth network, a ZigBee network, or another suitable personal area network. That said, in other embodiments, the network 510 could be realized as a wireless ad hoc network, a wireless local area network (WLAN), or local area network (LAN). The client device 506 includes or is coupled to a display device, such as a monitor, screen, or another conventional electronic display, capable of graphically presenting data and/or information pertaining to the physiological condition of the patient. The client device 506 also includes or is otherwise associated with a user input device, such as a keyboard, a mouse, a touchscreen, or the like, capable of receiving input data and/or other information from the user of the client device 506.

In some embodiments, a user, such as the patient, the patient's doctor or another healthcare provider, or the like, manipulates the client device 506 to execute a client application 508 that supports communicating with the medical device 502 via the network 510. In this regard, the client application 508 supports establishing a communications session with the medical device 502 on the network 510 and receiving data and/or information from the medical device 502 via the communications session. The medical device 502 may similarly execute or otherwise implement a corresponding application or process that supports establishing the communications session with the client application 508. The client application 508 generally represents a software module or another feature that is generated or otherwise implemented by the client device 506 to support the processes described herein. Accordingly, the client device 506 generally includes a processing system and a data storage element (or memory) capable of storing programming instructions for execution by the processing system, that, when read and executed, cause processing system to create, generate, or otherwise facilitate the client application 508 and perform or otherwise support the processes, tasks, operations, and/or functions described herein. Depending on the embodiment, the processing system may be implemented using any suitable processing system and/or device, such as, for example, one or more processors, central processing units (CPUs), controllers, microprocessors, microcontrollers, processing cores and/or other hardware computing resources configured to support the operation of the processing system described herein. Similarly, the data storage element or memory may be realized as a random-access memory (RAM), read only memory (ROM), flash memory, magnetic or optical mass storage, or any other suitable non-transitory short or long-term data storage or other computer-readable media, and/or any suitable combination thereof.

In one or more embodiments, the client device 506 and the medical device 502 establish an association (or pairing)

with one another over the network 510 to support subsequently establishing a point-to-point communications session between the medical device 502 and the client device 506 via the network 510. For example, in accordance with one embodiment, the network 510 is realized as a Bluetooth network, wherein the medical device 502 and the client device 506 are paired with one another (e.g., by obtaining and storing network identification information for one another) by performing a discovery procedure or another suitable pairing procedure. The pairing information obtained during the discovery procedure allows either of the medical device 502 or the client device 506 to initiate the establishment of a secure communications session via the network 510.

In one or more exemplary embodiments, the client application 508 is also configured to store or otherwise maintain an address and/or other identification information for the remote device 514 on the second network 512. In this regard, the second network 512 may be physically and/or logically distinct from the network 510, such as, for example, the Internet, a cellular network, a wide area network (WAN), or the like. The remote device 514 generally represents a server or other computing device configured to receive and analyze or otherwise monitor measurement data, event log data, and potentially other information obtained for the patient associated with the medical device 502. In exemplary embodiments, the remote device 514 is coupled to a database 516 configured to store or otherwise maintain data associated with individual patients. In practice, the remote device 514 may reside at a location that is physically distinct and/or separate from the medical device 502 and the client device 506, such as, for example, at a facility that is owned and/or operated by or otherwise affiliated with a manufacturer of the medical device 502. For purposes of explanation, but without limitation, the remote device 514 may alternatively be referred to herein as a server.

It should be noted that in some embodiments, some or all of the functionality and processing intelligence of the remote computing device 514 can reside at the medical device 502 and/or at other components or computing devices that are compatible with the patient monitoring system 500. In other words, the patient monitoring system 500 need not rely on a network-based or a cloud-based server arrangement as depicted in FIG. 5, although such a deployment might be the most efficient and economical implementation. These and other alternative arrangements are contemplated by this disclosure. To this end, some embodiments of the system 500 may include additional devices and components that serve as data sources, data processing units, and/or recommendation delivery mechanisms. For example, the system 500 may include any or all of the following elements, without limitation: computer devices or systems; patient monitors; healthcare provider systems; data communication devices; and the like.

Still referring to FIG. 5, the sensing element 504 generally represents the component of the patient monitoring system 500 that is configured to generate, produce, or otherwise output one or more electrical signals indicative of a physiological condition that is sensed, measured, or otherwise quantified by the sensing element 504. In this regard, the physiological condition of a patient influences a characteristic of the electrical signal output by the sensing element 504, such that the characteristic of the output signal corresponds to or is otherwise correlative to the physiological condition that the sensing element 504 is sensitive to. In exemplary embodiments, the sensing element 504 is realized as an interstitial glucose sensing element inserted at a location on the body of the patient that generates an output electrical signal having a current (or voltage) associated therewith that is correlative to the interstitial fluid glucose level that is sensed or otherwise measured in the body of the patient by the sensing element 504.

The medical device 502 generally represents the component of the patient monitoring system 500 that is communicatively coupled to the output of the sensing element 504 to receive or otherwise obtain the measurement data samples from the sensing element 504 (e.g., the measured glucose and characteristic impedance values), store or otherwise maintain the measurement data samples, and upload or otherwise transmit the measurement data to the server 514 via the client device 506. In one or more embodiments, the medical device 502 is realized as an infusion device 102, 202 configured to deliver a fluid, such as insulin, to the body of the patient. That said, in other embodiments, the medical device 502 could be a standalone sensing or monitoring device separate and independent from an infusion device (e.g., sensing arrangement 104, 204), such as, for example, a continuous glucose monitor (CGM), an interstitial glucose sensing arrangement, or similar device. It should be noted that although FIG. 5 depicts the medical device 502 and the sensing element 504 as separate components, in practice, the medical device 502 and the sensing element 504 may be integrated or otherwise combined to provide a unitary device that can be worn by the patient.

In exemplary embodiments, the medical device 502 includes a control module 522, a data storage element 524 (or memory), a communications interface 526, and a user interface 528. The user interface 528 generally represents the input user interface element(s) and/or output user interface element(s) associated with the medical device 502 (e.g., one or more user interface elements 240). The control module 522 generally represents the hardware, circuitry, logic, firmware and/or other component(s) of the medical device 502 that is coupled to the sensing element 504 to receive the electrical signals output by the sensing element 504 and perform or otherwise support various additional tasks, operations, functions and/or processes described herein. Depending on the embodiment, the control module 522 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In some embodiments, the control module 522 includes an analog-to-digital converter (ADC) or another similar sampling arrangement that samples or otherwise converts an output electrical signal received from the sensing element 504 into corresponding digital measurement data value. In other embodiments, the sensing element 504 may incorporate an ADC and output a digital measurement value.

The communications interface 526 generally represents the hardware, circuitry, logic, firmware and/or other components of the medical device 502 that are coupled to the control module 522 for outputting data and/or information from/to the medical device 502 to/from the client device 506. For example, the communications interface 526 may include or otherwise be coupled to one or more transceiver modules capable of supporting wireless communications between the medical device 502 and the client device 506. In exemplary embodiments, the communications interface 526 is realized as a Bluetooth transceiver or adapter configured to support Bluetooth Low Energy (BLE) communications.

In exemplary embodiments, the remote device 514 receives, from the client device 506, measurement data values associated with a particular patient (e.g., sensor glucose measurements, acceleration measurements, and the like) that were obtained using the sensing element 504, and the remote device 514 stores or otherwise maintains the historical measurement data in the database 516 in association with the patient (e.g., using one or more unique patient identifiers). Additionally, the remote device 514 may also receive, from or via the client device 506, meal data or other event log data that may be input or otherwise provided by the patient (e.g., via client application 508) and store or otherwise maintain historical meal data and other historical event or activity data associated with the patient in the database 516. In this regard, the meal data may include, for example, a time or timestamp associated with a particular meal event, a meal type or other information indicative of the content or nutritional characteristics of the meal, and an indication of the size associated with the meal. In exemplary embodiments, the remote device 514 also receives historical fluid delivery data corresponding to basal or bolus dosages of fluid delivered to the patient by an infusion device 102, 202. For example, the client application 508 may communicate with an infusion device 102, 202 to obtain insulin delivery dosage amounts and corresponding timestamps from the infusion device 102, 202, and then upload the insulin delivery data to the remote device 514 for storage in association with the particular patient. The remote device 514 may also receive geolocation data and potentially other contextual data associated with a device 502, 506 from the client device 506 and/or client application 508, and store or otherwise maintain the historical operational context data in association with the particular patient. In this regard, one or more of the devices 502, 506 may include a global positioning system (GPS) receiver or similar modules, components or circuitry capable of outputting or otherwise providing data characterizing the geographic location of the respective device 502, 506 in real-time.

The historical patient data may be analyzed by one or more of the remote device 514, the client device 506, and/or the medical device 502 to alter or adjust operation of an infusion device 102, 202 to influence fluid delivery in a personalized manner. In exemplary embodiments described herein, historical patient data is utilized to develop a pharmacokinetic/pharmacodynamic (PK/PD) model for individual patients supported by the patient monitoring system 500. For example, in one embodiment, for each individual patient, a "digital twin" that includes a patient-specific PK/PD model and a fixed profile of meal absorption rates as a function of time (as identified from the patient's historical data) is generated and utilized to personalize infusion device settings for that individual patient. In this context, a digital twin is a mathematical model or simulation of an individual patient that includes a set of differential equations derived from the patient's historical data that together define or describe the patient's blood glucose response to carbohydrate intake and insulin delivery. In this regard, the resulting patient-specific PK/PD model used for the digital twin represents the model that best fits the patient's historical sensor glucose measurement data for the period of time under evaluation used to generate the model. The "output" of the digital twin is a predicted blood glucose level or profile based on "inputs" that are likely to influence the patient's glycemic state, such as an amount of insulin delivered, an amount of carbohydrate consumed, and/or the like, in conjunction with the various patient-specific parameter values associated with the model. For example, each digital twin may be associated with a personalized and patient-specific set of values for various closed-loop control parameters (e.g., PID gain coefficient values, PID time constants, basal insulin delivery rates, carbohydrate ratios, insulin sensitivity factors, target glucose values, and the like), which may be unique to each individual patient.

Depending on the embodiment, the digital twin may be updated on a periodic basis (e.g., daily, weekly, or the like), at scheduled intervals, or in response to new or updated patient data being uploaded to the remote server 514 and/or database 516 (e.g., new or more recent sensor glucose measurement data samples, insulin delivery amounts, meal event log data, and the like). Additional details regarding the development of a digital twin are provided in U.S. patent application Ser. No. 16/386,104, filed Apr. 16, 2019, and incorporated by reference herein in its entirety. As described in greater detail below, in one or more exemplary embodiments, a cloud-based digital twin for an individual patient is managed and/or maintained by the remote server 514 and/or database 516 and utilized automatically configure and adjust settings, gains, and parameters for that patient's infusion device 502. That said, in alternative embodiments where the infusion device has sufficient processing capabilities, the creation, updating, and management of the digital twin may be implemented at the infusion device 502 in lieu of a cloud-based implementation.

Contextual Control Adjustments

Figure 6:
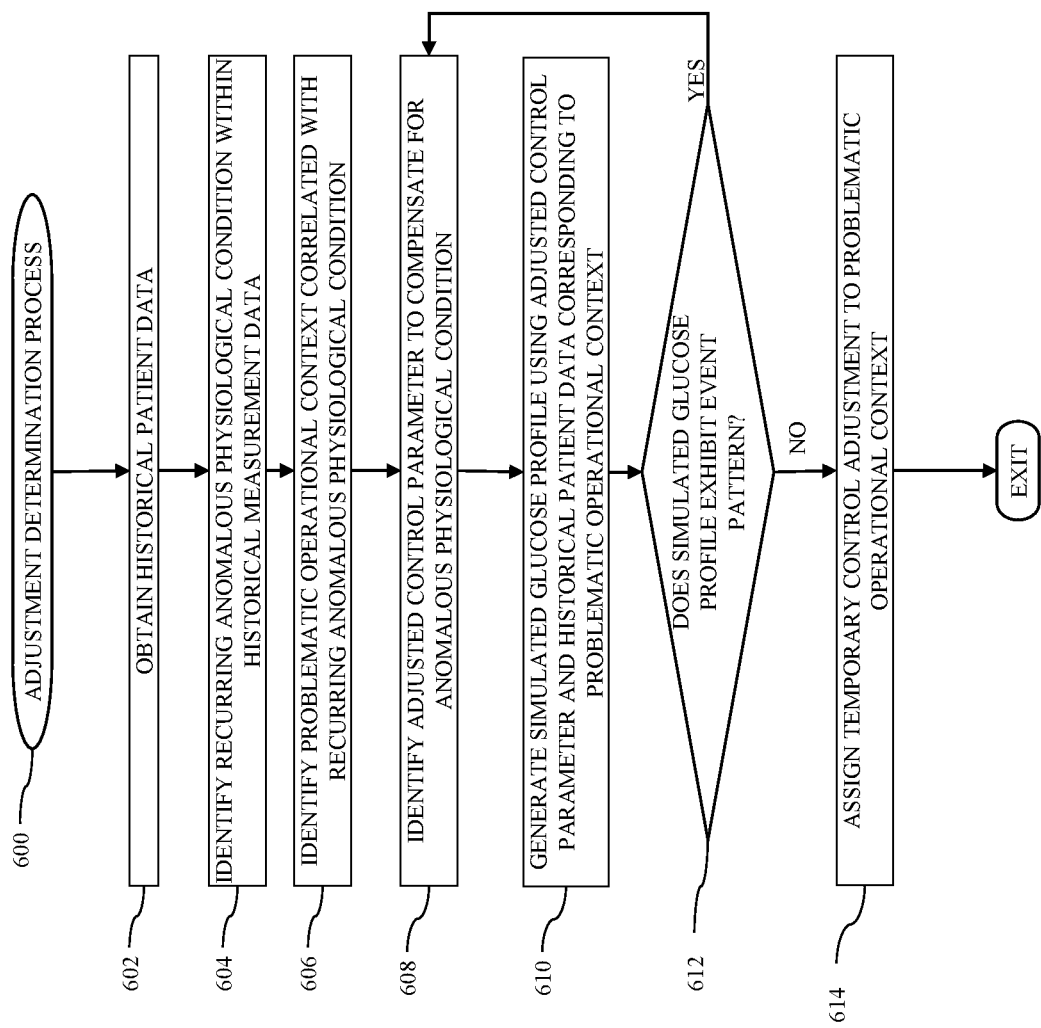
FIG. 6 is a flow diagram of an exemplary adjustment determination process suitable for implementation in connection with a closed-loop control system for a medical device in one or more exemplary embodiments.
Figure 7:
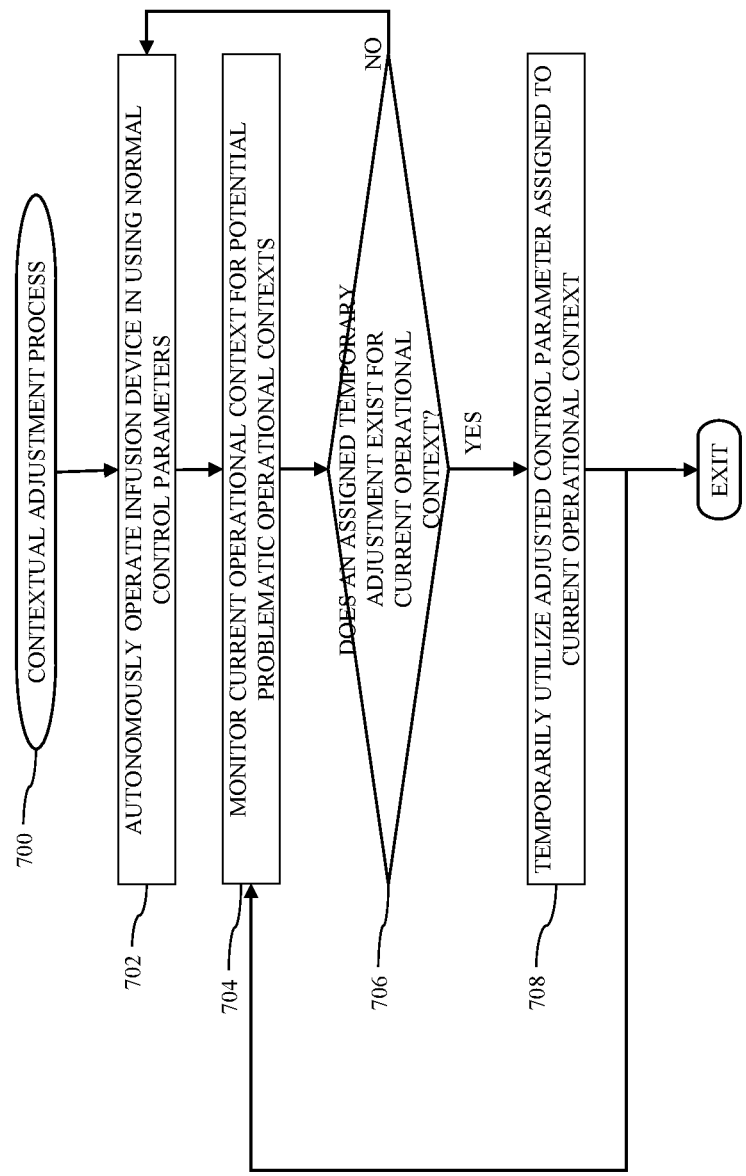
FIG. 7 is a flow diagram of an exemplary contextual adjustment process suitable for use with a medical device in connection with the adjustment determination process of FIG. 6 in one or more exemplary embodiments.

Referring now to FIGS. 6-7, in exemplary embodiments, a control parameter utilized by an autonomous operating mode of an infusion device is automatically adjusted for a temporary duration of time in a personalized manner and in real-time in response to detecting a particular operational context in order to influence fluid delivery during or around that operational context, and thereby mitigate or otherwise reduce the likelihood of an undesirable or anomalous physiological state. In this regard, the subject matter described herein accounts for so-called "hot spots," where other control personalization or optimizations such as those described above are unable to completely prevent a recurrent anomalous physiological state. For example, the local control algorithms implemented by the infusion device may be stateless or otherwise lack the data, ability or intelligence to account for recurrent "hot spot" scenarios, which may result in particular times of day or other operational contexts where the patient disproportionately experiences or exhibits an anomalous physiological state, condition or event.

Exemplary embodiments are described herein primarily in the context of adjusting the target (or reference) glucose value utilized by a closed-loop operating mode (e.g., the value at the input 402 to a closed-loop control system 400); however, the subject matter described herein is not limited to closed-loop control targets or closed-loop operating modes and may be implemented in an equivalent manner for other control parameters or other autonomous operating modes. For example, a basal-rate setting utilized by an open-loop operating mode that periodically and autonomously delivers fluid in accordance with the basal rate setting to effectuate a desired basal rate of infusion may be similarly adjusted in real-time in response to detecting a particular operational context during operation in the open-loop operating mode.

FIG. 6 depicts an exemplary adjustment determination process 600 for identifying operational contexts where a patient exhibits some recurrent physiological anomaly and determining corresponding control adjustments for mitigating physiological anomaly or otherwise reducing the likelihood of recurrence. The various tasks performed in connection with the adjustment determination process 600 may be performed by hardware, firmware, software executed by processing circuitry, or any combination thereof. For illustrative purposes, the following description refers to elements mentioned above in connection with FIGS. 1-5. For purposes of explanation, the adjustment determination process 600 may be described herein primarily in the context of being implemented at a remote server 514 in a patient monitoring system 500. It should be appreciated that the adjustment determination process 600 may include any number of additional or alternative tasks, the tasks need not be performed in the illustrated order and/or the tasks may be performed concurrently, and/or the adjustment determination process 600 may be incorporated into a more comprehensive procedure or process having additional functionality not described in detail herein. Moreover, one or more of the tasks shown and described in the context of FIG. 6 could be omitted from a practical embodiment of the adjustment determination process 600 as long as the intended overall functionality remains intact.

Depending on the embodiment, the adjustment determination process 600 may be performed on a periodic basis (e.g., daily, weekly, etc.), at a scheduled time of day (e.g., during an overnight period), in response to a manually initiating an update to his or her infusion device, or in response to more recent or updated patient data being available (e.g., in response to a batch of more recent measurement and delivery data being uploaded from an infusion device to a remote server and/or database). The adjustment determination process 600 receives or otherwise obtains patient data pertaining to preceding operation of the patient's infusion device and analyzes the patient's historical measurement data to detect or otherwise identify a pattern of a particular anomalous physiological event within the historical measurement data and an operational context that is correlated with the occurrence of the detected anomaly (tasks 602, 604, 606). For example, the patient's infusion device 502 and/or client device 506 may upload recent sensor glucose measurement data, insulin delivery data, event log data, contextual data, and the like to the remote device 514 for purposes of updating an individual's historical patient data maintained in the database 516. Thereafter, the remote device 514 analyzes the patient's historical sensor glucose measurement data to detect event patterns from within the historical sensor glucose measurement data that are correlated with particular operational contexts.

In one or more embodiments, the sensor glucose measurement values may be assigned to different operational context groups, which are then analyzed for anomalous glycemic states or conditions. For example, sensor glucose measurement values may be classified into different monitoring periods based on the timestamps associated with those values falling within the time period associated with the respective monitoring period(s) (e.g., measurement values having timestamps between 12 PM and 3 PM may be classified into a post-lunch monitoring period). Additionally, sensor glucose measurement values may be further classified into different groups based on the time of day, or other contextual data contemporaneous to the respective sensor glucose measurement values. For example, sensor glucose measurement values having substantially the same or common contemporaneous geographic location data associated therewith (e.g., measurement values from within a threshold distance of a patient's home) may be grouped into a particular operational context associated with that geographic location. Likewise, sensor glucose measurement values having substantially the same or common contemporaneous lifestyle activity associated therewith may be grouped together. Various embodiments may also analyze the patient's meal data, event log data, auxiliary measurement data (e.g., from sensing arrangements 206, 208), and the like to categorize or classify sensor glucose measurement values into different operational contexts corresponding to different lifestyle events or activities (e.g., mealtime, post-meal, sleeping, exercising, stress, menstruation, or the like). In this regard, the subject matter is not limited to any particular number, logic, or manner for categorizing or classifying the patient's historical sensor glucose measurement data into different operational context groups based on any number or combination of contemporaneous or concurrent auxiliary measurement data, delivery data, location data, meal data, exercise data, event log data or other contextual data indicative of a concurrent patient behavior, activity, or contextual state.

In such embodiments, after the sensor measurement values are classified into one or more operational context groups, the sensor measurement values within each operational context group may be analyzed with respect to the various event detection criteria to identify event patterns associated with the respective group. For example, the sensor measurement values may be compared to a glucose threshold value to identify a number of times or cumulative duration of time that the sensor measurement values violated the glucose threshold value within the monitoring period, and a corresponding event pattern may be detected when the number or duration of time is greater than a corresponding detection threshold. For example, a hypoglycemic (or low glucose) event pattern may be identified when sensor measurement values fall below a lower glucose threshold value (e.g., 70 mg/dL) during more than 50% of the days or instances of the particular operational context. Similarly, a hyperglycemic (or high glucose) event pattern may be identified when sensor measurement values are above an upper glucose threshold value (e.g., 150 mg/dL) by greater than a particular number or a duration of time with sufficient frequency. In this regard, it should be noted that there are any number of different detection thresholds that may be utilized to detect event patterns with the desired degree of severity and/or frequency, and the subject matter described herein is not intended to be limited to any particular thresholds or logic for detecting or identifying event patterns associated with different operational contexts. Additionally, it should be noted that other glucose measurement metrics (e.g., sensor glucose measurement rate of change values, etc.) may be assigned to different operational context groups and analyzed for anomalous glycemic states or conditions in an equivalent manner, and the subject matter described herein is not limited to any particular type of sensor glucose measurement data for analysis.

In yet other embodiments, machine learning or artificial intelligence may be applied to the patient's historical data to identify correlations between a particular physiological state or condition and corresponding contextual variables. For example, the remote server 514 may utilize machine learning to determine which combination of historical delivery data, historical auxiliary measurement data (e.g., historical acceleration measurement data, historical heart rate measurement data, and/or the like), historical event log data, historical geolocation data, and other historical or contextual data are correlated to or predictive of the occurrence of a particular glycemic state, condition or event and identify the degree or correlation between those variables and the glycemic state. In some embodiments, the remote server 514 may determine an equation, function, or model for calculating the likelihood or probability of the particular glycemic state based on a correlative set of input contextual variables. Thus, a particular combination of auxiliary measurement data, delivery data, geographic location, patient behavior or activities, and the like may be mapped to a particular glycemic condition. It should be noted that the contextual variables that are predictive of or correlative for a particular patient may vary from other users. It should also be noted that any number of different machine learning techniques may be utilized by the remote device 514 to determine what combination of contextual variable states are predictive for a current patient of interest, such as, for example, artificial neural networks, linear models, general linear models, generalized linear models, search trees, genetic programming, support vector machines, Bayesian networks, probabilistic machine learning models, or other Bayesian techniques, fuzzy logic, heuristically derived combinations, or the like.

In the illustrated embodiment, after identifying a correlation between an operational context and a recurring anomalous glycemic state or condition, the adjustment determination process 600 continues by identifying an adjusted control parameter value to compensate for that anomalous glycemic state, generating a simulated glucose profile for the patient using the adjusted control parameter values and the recent patient data for the correlated operational context, and determining whether the simulated glucose profile exhibits the anomalous glycemic state or condition (tasks 608, 610, 612). In this regard, the adjustment determination process 600 may repeat the loop defined by tasks 608, 610 and 612 to iteratively adjust a control parameter value until the anomalous glycemic state or condition is not exhibited by the resulting simulated glucose profile. When the adjusted control parameter value sufficiently compensates for the anomalous glycemic state or condition, the adjustment determination process 600 assigns or otherwise associates the adjusted control parameter value with the problematic operational context for subsequent usage during that operational context (task 614), as described in greater detail below in the context of FIG. 7.

For example, as described above, in one or more embodiments, the remote server 514 builds or otherwise creates a model associated with the patient that can be utilized to generate a simulated glucose profile for the patient based on the patient's historical event log data (e.g., the recent meal data, exercise information, sleep information, and/or the like). In connection with the adjustment determination process 600 in the context of a closed-loop operating mode, the remote server 514 may adjust the closed-loop control target value (e.g., the patient's target glucose or set point for the closed-loop mode at input 402) to be utilized during periods of the patient's historical data where the operational context is correlated with the recurrent anomalous glycemic state or condition. For example, in exemplary embodiments where a digital twin for the patient is maintained (e.g., in the database 516), the remote server 514 utilizes that patient's particular PK/PD model to generate predicted sensor glucose measurement values that result from simulated operation of the patient's infusion device 502 using the adjusted closed-loop control target value for a period of time corresponding to the problematic operational context using the patient's historical meal data, exercise data, bolus data, sleep data, and the like. In this regard, in some embodiments, predicted sensor glucose measurement values are determined using the patient's historical meal data, exercise data, bolus data, sleep data, and the like for prior instances of the problematic operational context when the anomalous glycemic state or condition occurred to determine whether or not the adjusted closed-loop control target value likely would have been sufficient to mitigate or prevent the anomalous glycemic state or condition.

For example, for a patient exhibiting a hyperglycemic event pattern during a post-lunch period between 2 PM and 3 PM, that patient's personalized PK/PD model may be utilized to simulate what the patient's sensor glucose measurement values likely would have been during preceding instances of operation between 2 PM and 3 PM using a temporarily reduced closed-loop control target value during the 2 PM to 3 PM time period with the patient's historical meal data, exercise data, bolus data, sleep data, and the like associated with those preceding instances of operation between 2 PM and 3 PM. In this regard, if the simulated glucose profile is maintained below a hyperglycemic threshold or otherwise does not exhibit a hyperglycemic event pattern, that reduced closed-loop control target value may be assigned or otherwise associated with the 2 PM to 3 PM operational context. For example, the reduced closed-loop control target value may be stored or maintained in a lookup table that maintains associations between problematic operational contexts and their assigned temporary control parameter adjustment for the respective operating mode. Conversely, if the simulated glucose profile with the reduced closed-loop control target still exhibits a hyperglycemic event pattern, the adjustment determination process 600 may continually reduce the closed-loop control target value and generate an updated simulated glucose profile using the updated closed-loop control target value until the simulated glucose profile is maintained below a hyperglycemic threshold or otherwise does not exhibit a hyperglycemic event pattern. In this regard, the adjustment determination process 600 may iteratively increase or decrease the closed-loop control target value by some fixed percentage (e.g., 5%) or fixed amount (e.g., 5 mg/dL) until arriving at a simulated glucose profile that indicates that the anomalous glycemic state is likely to be mitigated. In a similar manner, for an open-loop mode, the adjustment determination process 600 may iteratively increase or decrease a basal rate setting by a fixed percentage or a fixed amount until the resulting simulated glucose profile does not exhibit a glycemic anomaly.

It should be noted that in some embodiments, the adjustment determination process 600 may generate multiple different simulated glucose profiles for multiple different control parameter adjustments and apply cost function or perform some other optimization to identify an optimal adjusted value for the control parameter. For example, a cost function could be constructed such that the resulting cost is influenced by the relationship between the simulated glucose values and a target glucose value, the duration during which the simulated glucose values are within a desired range of values (e.g., within some threshold of the normal target or original target glucose value), the amount of insulin delivered using the adjusted control parameter value, and the like. The adjustment determination process 600 may then select or otherwise identify, from among the subset of potential closed-loop control targets that sufficiently mitigate or reduce the likelihood of recurrence of an anomalous glycemic state, the potential adjusted closed-loop control target that achieves the minimum cost as the optimal closed-loop control target to be assigned to the particular problematic operational context. Thus, the resulting adjusted closed-loop control target may not only mitigate or reduce the likelihood of recurrence of a particular glycemic event pattern, the closed-loop control target may also optimize some other aspect of insulin delivery or glycemic control during that particular operational context.

FIG. 7 depicts an exemplary contextual adjustment process 700 for autonomously operating an infusion device in connection with the adjustment determination process 600 of FIG. 6 to temporarily adjust a control parameter to mitigate or otherwise reduce the likelihood of a physiological anomaly recurring during a particular operational context. The various tasks performed in connection with the contextual adjustment process 700 may be performed by hardware, firmware, software executed by processing circuitry, or any combination thereof. For illustrative purposes, the following description refers to elements mentioned above in connection with FIGS. 1-5. For purposes of explanation, the contextual adjustment process 700 may be described herein primarily in the context of being implemented at an infusion device 102, 202, 502. It should be appreciated that the contextual adjustment process 700 may include any number of additional or alternative tasks, the tasks need not be performed in the illustrated order and/or the tasks may be performed concurrently, and/or the contextual adjustment process 700 may be incorporated into a more comprehensive procedure or process having additional functionality not described in detail herein. Moreover, one or more of the tasks shown and described in the context of FIG. 7 could be omitted from a practical embodiment of the contextual adjustment process 700 as long as the intended overall functionality remains intact.

In exemplary embodiments, the contextual adjustment process 700 is implemented or otherwise performed by a control system 220, 300, 522 at an infusion device 102, 202, 502 after the remote server 514 performs the adjustment determination process 600 to identify problematic operational contexts and corresponding control adjustments for a patient. For example, after the remote server 514 performs the adjustment determination process 600 to identify different operational contexts that may be problematic for the patient and determine and assign corresponding control adjustments to those operational contexts, the remote device 514 may push, transmit or otherwise provide indication of those operational contexts and their associated operating modes and control parameter adjustments to the infusion device 102, 202, 502, either directly or via an intermediary client device 506, over the network 512. For example, the lookup table of operational contexts and control parameter adjustments may be pushed or otherwise provided to the infusion device 102, 202, 502 for local storage (e.g., in memory 306, 524). In other embodiments, the infusion device 102, 202, 502 may attempt to download or otherwise obtain the identified problematic operational contexts and determined control parameter adjustments associated with a particular operating mode from the remote device 514 and/or database 516 upon entering that operating mode.

The contextual adjustment process 700 begins by autonomously operating the infusion device to deliver fluid in accordance with the normal control parameters for an autonomous operating mode (task 702). For example, in a closed-loop operating mode, the pump control system 220, 300 may periodically determine dosage commands in accordance with a closed-loop control system 400 based on the difference between the patient's current or real-time sensed glucose measurement value from an interstitial glucose sensing arrangement 204, 504 provided at input 404 and a normal target glucose value at input 402, which may have been manually set by the patient or determined based on the patient's historical data as described above. Similarly, in an open-loop operating mode, the pump control system 220, 300 may periodically provide dosage command corresponding to a normal or default basal rate setting for the open-loop operating mode, which similarly may have been manually set by the patient or determined based on the patient's historical data.

The contextual adjustment process 700 continually monitors or analyzes the current operational context to detect or otherwise identify when the current operational context corresponds to a previously problematic operational context that has an adjusted control parameter assigned or otherwise associated therewith (tasks 704, 706). In this regard, the pump control system 220, 300 may continually monitor the current time of day, the current day of the week, the current geographic location, the auxiliary measurement data from various other sensing arrangements 206, 208, meal or other bolus wizard data, activity or event log data, and the like substantially in real-time to identify or otherwise determine whether the current or recent combination of contextual variable states matches or otherwise corresponds to a operational context that was previously problematic for the patient. In the absence of identifying a potentially problematic operational context, the contextual adjustment process 700 maintains autonomous operation in accordance with the normal or default control parameters (task 702).

In response to detecting or otherwise determining that the current operational context matches or otherwise corresponds to a potentially problematic operational context, the contextual adjustment process 700 automatically alters implementation of the autonomous operating mode to temporarily utilize the adjusted control parameter value that is assigned to or otherwise associated with that operational context (task 708). In this regard, the pump control system 220, 300 may utilize a lookup table to identify an adjusted control parameter value associated with a particular combination of contextual variables corresponding to the current operational context. For example, if the pump control system 220, 300 is autonomously operating the infusion device 102, 202, 502 in a closed-loop operating mode for a patient that has previously exhibited a hyperglycemic event pattern between 2 PM and 3 PM while in the closed-loop operating mode, in response to detecting the current time of day is between 2 PM and 3 PM, the pump control system 220, 300 may automatically retrieve or otherwise obtain the adjusted closed-loop control target associated with the 2-3 PM time period and utilize that reduced closed-loop control target glucose value at the input 402 in lieu of the normal target glucose value or set point. For example, the target glucose value at input 402 may be adjusted from a normal value of 120 mg/dL to 100 mg/dL. As a result, the closed-loop control system 400 will determine greater dosage commands (or increase the basal delivery rate) relative to what the normal target glucose value would achieve for the same sensed glucose measurement value provided at input 404, thereby reducing the likelihood or severity of any hyperglycemic event.

As another example, for a patient that has previously exhibited a hypoglycemic event pattern during exercise having a particular duration or level of intensity, the pump control system 220, 300 may automatically detect exercise of that duration or intensity based on a combination of acceleration measurement data from the acceleration sensing arrangement 208 and heart rate measurement data from a heart rate sensing arrangement 206. In response, the pump control system 220, 300 may automatically retrieve or otherwise obtain the adjusted closed-loop control target associated with that duration or intensity of exercise and utilize that increased closed-loop control target glucose value at the input 402 in lieu of the normal target glucose value or set point. For example, the target glucose value at input 402 may be adjusted from a normal value of 120 mg/dL to 150 mg/dL, which results in the closed-loop control system 400 determining reduced dosage commands (or decreasing the basal delivery rate) relative to what the normal target glucose value would achieve for the same sensed glucose measurement value provided at input 404, thereby reducing the likelihood or severity of any hyperglycemic event.

It should be noted that the contextual adjustment process 700 can also be implemented in an equivalent manner for an open-loop operating mode. For example, for a patient that has previously exhibited a hyperglycemic event pattern between 2 PM and 3 PM while in the open-loop operating mode, in response to detecting the current time of day is between 2 PM and 3 PM, the pump control system 220, 300 may automatically retrieve or otherwise obtain the adjusted basal rate associated with the 2-3 PM time period and utilize that increased basal rate in lieu of the normal or default basal rate to thereby reduce the likelihood or severity of any hyperglycemic event. Similarly, in response to detecting a particular type of exercise for which the patient has previously exhibited a hypoglycemic event pattern, the pump control system 220, 300 may automatically retrieve or otherwise obtain the adjusted basal rate associated with the detected exercise and utilize a decreased basal rate in lieu of the normal or default basal rate to thereby reduce the likelihood or severity of any hypoglycemic event.

It should be noted that there are any different number or combination of contextual variables that may be utilized to identify or otherwise differentiate problematic operational contexts relative to those where the normal or default control parameters are utilized. For example, if a patient only exhibits a hypoglycemic event pattern in connection with exercise on a particular day of the week (e.g., Saturday) at a particular time of day (e.g., between 9 AM and 12 PM), the pump control system 220, 300 will maintain the normal closed-loop control parameters even if that particular duration, intensity, or type of exercise is detected provided that the current time is not between 9 AM and 12 PM and that the current day of the week is not Saturday. In this manner, the combination of the adjustment determination process 600 and the contextual adjustment process 700 allows for the autonomous operating mode to automatically adapt to handle specific operational contexts that have been previously problematic for the patient but are somewhat limited in their duration or frequency, such that the personalization of control parameters (e.g., PID gain coefficient values, PID time constants, basal insulin delivery rates, carbohydrate ratios, insulin sensitivity factors, target glucose values) may be unable to account for such limited scenarios. Thus, potentially anomalous glycemic events may be mitigated or prevented automatically without requiring any manual intervention.

Still referring to FIG. 7, in the illustrated embodiment, the contextual adjustment process 700 continually monitors or analyzes the current operational context to detect or otherwise identify when the current operational context no longer corresponds to a previously problematic operational context before reverting back to the normal control parameters (tasks 704, 706, 708). In this regard, the adjusted control parameter may be maintained temporarily until the operational context changes. For example, if the patient that has previously exhibited a hyperglycemic event pattern between 2 PM and 3 PM, the pump control system 220, 300 may maintain the adjusted closed-loop control target associated with the 2-3 PM time period at the input 402 until the current time of day is after 3 PM, at which point the pump control system 220, 300 may automatically revert the control target at input 402 back to the normal target glucose value or set point. Similarly, if the patient that has previously exhibited a hypoglycemic event pattern during or around a particular exercise event, the pump control system 220, 300 may maintain the increased closed-loop control target value at the input 402 for the duration of the exercise or a particular amount of time after the exercise event has elapsed (which may be determined based on the patient's historical data) before may automatically reverting the control target at input 402 back to the normal target glucose value or set point. In other embodiments, the patient's sensor glucose measurement values (and/or the rate of change thereof) may be continually monitored while the adjusted closed-loop control target is utilized until the patient's sensor glucose measurement values satisfy one or more criteria for reverting to the normal control parameters. For example, the pump control system 220, 300 may monitor the patient's sensor glucose measurement value to detect or otherwise identify when the patient's sensor glucose measurement value(s) are within a threshold of a normal closed-loop control target or otherwise within a desired range of values and/or the patient's sensor glucose rate of change is less than a threshold amount. Thus, the contextual adjustment process 700 may dynamically revert to normal operations in response to detecting satisfaction of certain criteria in real-time.

For the sake of brevity, conventional techniques related to glucose sensing and/or monitoring, bolusing, closed-loop glucose control, patient modeling, cost functions, optimization and related mathematical concepts, and other functional aspects of the subject matter may not be described in detail herein. In addition, certain terminology may also be used in the herein for the purpose of reference only, and thus is not intended to be limiting. For example, terms such as "first", "second", and other such numerical terms referring to structures do not imply a sequence or order unless clearly indicated by the context. The foregoing description may also refer to elements or nodes or features being "connected" or "coupled" together. As used herein, unless expressly stated otherwise, "coupled" means that one element/node/feature is directly or indirectly joined to (or directly or indirectly communicates with) another element/node/feature, and not necessarily mechanically.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A method of automatically adjusting a control parameter for an operating mode of an infusion device, the method comprising:
    monitoring a current operational context during autonomous operation of the infusion device to deliver fluid to a patient in accordance with the operating mode using an initial value for the control parameter; and
in response to identifying an adjusted value for the control parameter associated with the current operational context:
  autonomously operating the infusion device to deliver the fluid to the patient in accordance with the operating mode using the adjusted value for the control parameter in lieu of the initial value; and
  thereafter reverting the control parameter to the initial value.

2. The method of claim 1, wherein the operating mode comprises a closed-loop operating mode and the control parameter comprises a closed-loop control target, wherein autonomously operating the infusion device in accordance with the operating mode using the adjusted value comprises autonomously determining dosage commands for delivering the fluid to the patient based on a difference between a measurement value and the adjusted value for the closed-loop control target.

3. The method of claim 1, wherein the operating mode comprises an open-loop operating mode and the control parameter comprises a basal rate setting, wherein autonomously operating the infusion device in accordance with the open-loop operating mode using the adjusted value comprises autonomously determining dosage commands in accordance with the adjusted value for the basal rate setting.

4. The method of claim 1, wherein:
monitoring current operational context comprises monitoring measurement data from one or more auxiliary sensing arrangements; and
identifying the adjusted value comprises identifying the measurement data corresponds to an operational context assigned to the adjusted value.

5. The method of claim 1, wherein:
monitoring current operational context comprises monitoring a current time of day; and
identifying the adjusted value comprises identifying the current time of day corresponds to an operational context assigned to the adjusted value.

6. The method of claim 1, wherein:
monitoring current operational context comprises monitoring an activity by the patient; and
identifying the adjusted value comprises identifying the activity corresponds to an operational context assigned to the adjusted value.

7. The method of claim 1, further comprising:
determining a simulated profile of a physiological condition of the patient based at least in part on historical data associated with the patient during a prior instance of an operational context associated with an anomalous state of the physiological condition using the adjusted value for the control parameter of the operating mode; and
assigning adjusted value to the operational context when the simulated profile mitigates the anomalous state of the physiological condition, wherein identifying the adjusted value comprises identifying the current operational context corresponds to the operational context having the adjusted value assigned thereto.

8. The method of claim 7, wherein the operating mode comprises a closed-loop operating mode and the control parameter comprises a closed-loop control target for the physiological condition influenced by the fluid, wherein autonomously operating the infusion device in accordance with the operating mode using the adjusted value comprises autonomously determining dosage commands for delivering the fluid to the patient based on a difference between one or more measurements of the physiological condition of the patient and the adjusted value for the closed-loop control target.

9. The method of claim 8, wherein reverting the control parameter to the initial value comprises autonomously determining dosage commands for delivering the fluid to the patient based on a difference between one or more subsequent measurement values and the initial value for the closed-loop control target when the current operational context no longer corresponds to the operational context associated with the anomalous state of the physiological condition.

10. A method of autonomously delivering fluid using an infusion device, the method comprising:
determining initial commands for delivering the fluid based at least in part on a difference between one or more measurement values of a physiological condition in a body of a patient and a normal target value for the physiological condition in the body of the patient; and
in response to detecting a current operational context corresponds to an operational context previously associated with an anomalous state of the physiological condition of the patient:
  determining adjusted commands for delivering the fluid based at least in part on an updated difference between one or more subsequent measurement values of the physiological condition in the body of the patient and an adjusted target value for the physiological condition associated with the operational context in lieu of the normal target value; and
  thereafter determining subsequent commands for delivering the fluid based at least in part on the normal target value.

11. The method of claim 10, further comprising monitoring measurement data from one or more auxiliary sensing arrangements to identify the current operational context based at least in part on the measurement data.

12. The method of claim 10, wherein determining the adjusted commands comprises determining the adjusted commands for a temporary duration of time when the current operational context corresponds to the operational context.

13. The method of claim 10, wherein:
the fluid comprises insulin;
the physiological condition comprises a glucose level;
the anomalous state of the physiological condition comprises a hyperglycemic event; and
the adjusted target value is less than the normal target value.

14. The method of claim 10, wherein:
the fluid comprises insulin;
the physiological condition comprises a glucose level;
the anomalous state of the physiological condition comprises a hypoglycemic event; and
the adjusted target value is greater than the normal target value.

15. The method of claim 10, wherein detecting the current operational context corresponds to the operational context comprises identifying an entry in a lookup table matching the current operational context, wherein the lookup table comprises a plurality of entries and each entry of the plurality of entries corresponds to a respective problematic operational context previously associated with a respective anomalous state of the physiological condition of the patient.

16. The method of claim 10, further comprising:
determining one or more simulated profiles of the physiological condition of the patient based at least in part on historical data corresponding to the anomalous state of the physiological condition of the patient during the operational context using one or more adjusted values for a target value for a closed-loop operating mode of the infusion device; and
assigning an adjusted value of the one or more adjusted values to the operational context when the respective simulated profile associated with the adjusted value mitigates the anomalous state of the physiological condition, wherein determining the adjusted commands comprises determining the adjusted commands based at least in part on the updated difference between the one or more subsequent measurement values and the adjusted value assigned to the operational context in lieu of the normal target value.

17. An infusion system comprising:
an actuation arrangement operable to deliver fluid to a patient;
a data storage element to maintain associations between adjusted control parameter values and historical operational contexts for the patient; and
a control system coupled to the actuation arrangement and the data storage element to monitor a current operational context during autonomous operation of the actuation arrangement to deliver the fluid to the patient in accordance with an operating mode using an initial value for a control parameter and in response to determining the current operational context matches a historical operational context of the historical operational contexts, temporarily determine commands for autonomously operating the actuation arrangement in accordance with the operating mode using a respective adjusted control parameter value associated with the historical operational context instead of the initial value.

18. The infusion system of claim 17, wherein:
the operating mode comprises a closed-loop operating mode;
the control parameter comprises a closed-loop control target;
the initial value comprises a normal closed-loop control target value;
the respective adjusted control parameter value associated with the historical context comprises an adjusted closed-loop control target value different from the normal closed-loop control target value; and
the control system temporarily determines commands for autonomously operating the actuation arrangement based at least in part on a difference between a measurement value for a physiological condition of the patient and the adjusted closed-loop control target value.

19. The infusion system of claim 17, wherein:
the operating mode comprises an open-loop operating mode;
the control parameter comprises an open-loop basal rate setting;
the initial value comprises a normal basal rate;
the respective adjusted control parameter value associated with the historical context comprises an adjusted basal rate different from the normal basal rate; and
the control system temporarily determines commands for autonomously operating the actuation arrangement to provide the adjusted basal rate of infusion.

20. The infusion system of claim 17, further comprising an auxiliary sensing arrangement to provide auxiliary measurement data, wherein the control system is coupled to the auxiliary sensing arrangement to determine the current operational context based at least in part on the auxiliary measurement data.

* * * * *